United States Patent
Ieda et al.

(10) Patent No.: US 7,799,203 B2
(45) Date of Patent: Sep. 21, 2010

(54) GAS DETECTION APPARATUS, GAS-SENSOR CONTROL CIRCUIT USED FOR GAS DETECTION APPARATUS, AND INSPECTION METHOD FOR GAS DETECTION APPARATUS

(75) Inventors: Norikazu Ieda, Aichi (JP); Hiroshi Inagaki, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1181 days.

(21) Appl. No.: 11/391,366

(22) Filed: Mar. 29, 2006

(65) Prior Publication Data

US 2006/0219553 A1  Oct. 5, 2006

(30) Foreign Application Priority Data

Mar. 30, 2005  (JP)  ............... 2005-098243

(51) Int. Cl.
  *G01N 27/409*  (2006.01)
  *G01N 27/41*  (2006.01)
(52) U.S. Cl. ............ 205/784.5; 205/781; 73/23.31; 204/401; 204/406; 204/424
(58) Field of Classification Search ........... 204/401, 204/424–429, 406, 421–423; 123/672–697; 73/23.31; 205/784.5, 781
See application file for complete search history.

(56) References Cited

U.S. PATENT DOCUMENTS

| | | | |
|---|---|---|---|
| 4,167,396 A * | 9/1979 | Kondo et al. ............... | 123/695 |
| 4,818,362 A | 4/1989 | Asakura et al. | |
| 5,554,951 A * | 9/1996 | Gough ............... | 327/337 |
| 5,810,997 A | 9/1998 | Okazaki et al. | |
| 7,170,731 B2 | 1/2007 | Wagner | |
| 2004/0238378 A1 | 12/2004 | Kumazawa et al. | |

FOREIGN PATENT DOCUMENTS

| | | |
|---|---|---|
| EP | 0 884 587 A1 | 12/1998 |
| EP | 0 937 979 A2 | 8/1999 |

(Continued)

OTHER PUBLICATIONS

Makoto Nakae et al.; "Development of Planar Air Fuel Ratio Sensor"; SAE Technical Paper Series 2002-01-0474; SAE 2002 World Congress; 2002 Society of Automotive Engineers, Inc.

*Primary Examiner*—Alexa D Neckel
*Assistant Examiner*—Jennifer Dieterle
(74) *Attorney, Agent, or Firm*—Sughrue Mion, PLLC

(57) ABSTRACT

A gas detection apparatus including a gas sensor element and a gas-sensor control circuit. The gas sensor element includes at least one sensor cell including a solid electrolyte member and a pair of electrodes, and external connection terminals electrically connected to the electrodes. The gas-sensor control circuit includes control terminals electrically connected to respective external connection terminals of the gas sensor element, an inspection current supply circuit for supplying an inspection current to an inspected terminal, which is a control terminal to be inspected for presence or absence of a short circuit to a predetermined potential, an inspection potential measurement circuit for measuring the potential of the inspected terminal, and an uninspected terminal impedance increasing circuit for increasing the impedance of the gas-sensor control circuit as viewed from an uninspected terminal, which is a control terminal other than the inspected terminal.

26 Claims, 12 Drawing Sheets

FOREIGN PATENT DOCUMENTS

| | | |
|---|---|---|
| FR | 2 846 161 | 4/2004 |
| JP | 9-61397 | 3/1997 |
| JP | 2003-90821 | 3/2003 |
| JP | 2003-090821 * | 3/2003 |
| JP | 2003-97342 A | 4/2003 |

* cited by examiner

GAS DETECTION APPARATUS, GAS-SENSOR CONTROL CIRCUIT USED FOR GAS DETECTION APPARATUS, AND INSPECTION METHOD FOR GAS DETECTION APPARATUS

BACKGROUND OF THE INVENTION

1. Field of the Invention

The present invention relates to a gas detection apparatus which includes a gas sensor element and which detects the presence/absence or concentration of a specific gas in a gas to be measured (hereinafter referred to as "measured gas"), and to a gas-sensor control circuit for controlling the gas detection apparatus. Moreover, the present invention relates to an inspection method for inspecting the gas detection apparatus for the presence of short circuits.

2. Description of the Related Art

In a known combustion control scheme for an internal combustion engine such as a gasoline engine, in accordance with the concentration of a specific gas contained in exhaust gas, the quantity of fuel supplied to the engine is subject to feedback control so as to control the air-fuel ratio of a gas mixture of air and fuel supplied to the engine. The object of such control is to reduce CO, $NO_x$, and HC emissions in the exhaust gas.

A known gas sensor element used for such air-fuel ratio control is a full range air-fuel-ratio sensor (hereinafter also referred to as a "UEGO sensor") in which two sensor cells (a pump cell and a detection cell) each including a solid electrolyte member formed of, for example, zirconia, and two electrodes disposed on opposite surfaces thereof are disposed to face each other. This UEGO sensor includes these two sensor cells, and a measurement chamber which communicates with a measured space (a space where measurement is performed) via a diffusion resistance. The UEGO sensor can detect the oxygen concentration of a measured gas introduced into the measurement chamber via the diffusion resistance.

Incidentally, when a portion (e.g., a wire or a connector) which is electrically connected to an electrode of a detection cell is, for any reason, short-circuited to the power-source potential or the ground potential, current flows through the detection cell in an improper direction, and so-called blackening, which is a phenomenon in which oxygen ions disappear from the solid electrolyte constituting the detection cell, occurs, so that the measurement characteristics of the gas sensor element deteriorate.

Further, a gas sensor element is known in which one of electrodes which constitute a detection cell is disposed outside a measurement chamber in a closed space isolated from the outside, and a small, constant current is supplied to the detection cell so as to cause the closed space to function as a reference oxygen chamber. In such a gas sensor, when the electrode disposed in the closed space or a portion which is electrically connected to the electrode is short-circuited to ground, excessive current flows through the detection cell, and oxygen is excessively pumped. As a result, the pressure of the reference oxygen chamber increases, thereby possibly rupturing the gas sensor element.

In order to cope with such a problem, a gas detection apparatus has been proposed which uses a gas sensor element of the above-described type and which performs diagnosis as to the presence or absence of short-circuiting of the wire, etc., to ground or the power-source.

In the gas detection apparatus disclosed in Japanese Patent Application Laid-Open (kokai) No. 2003-90821, the potentials of portions which are electrically connected to the electrodes of the sensor cells of the gas sensor apparatus are measured for such short-circuit inspection. A determination as to, for example, whether the measured potentials fall within a predetermined range is made so as to determine whether any of the portions electrically connected to the electrodes of the sensor cells is short-circuited to the power-source or to ground.

However, the gas detection apparatus disclosed in the publication detects anomalous conditions, such as a short-circuit, in a state in which the gas detection apparatus is performing a predetermined operation after activation of the gas sensor element. Therefore, the gas detection apparatus cannot cope with a problem in which current flowing in an improper direction adversely affects the gas sensor element at the time of startup of the gas detection apparatus. Specifically, in a case where, for some reason, a portion electrically connected to one electrode of the detection cell is short-circuited to ground before startup, when the gas detection apparatus, including a circuit which is connected to the detection cell for short-circuit inspection, is started, current immediately starts to flow in an improper (reverse) direction through the detection cell, from an output terminal of the circuit connected to the other electrode of the detection cell to the one electrode short-circuited to ground. Therefore, even if the gas detection apparatus detects that the portion electrically connected to the one electrode is short-circuited to ground and immediately cuts off power to the gas detection apparatus, the gas detection apparatus cannot prevent an adverse effect on the gas sensor element exerted due to current which has already flowed through the detection cell in an improper direction before the power is cut off.

SUMMARY OF THE INVENTION

In view of the foregoing, an object of the present invention is to provide a gas detection apparatus which can inspect whether a wiring line, terminal, etc., of a gas sensor element is short-circuited to a certain potential such as power-source potential or ground potential, while preventing, during the short-circuit inspection, current from excessively flowing through a sensor cell or in an improper (reverse) direction, to thereby prevent damage or other adverse effect on the sensor cell.

Another object of the present invention is to provide a gas-sensor control circuit for controlling the gas detection apparatus.

Still another object of the present invention is to provide a method for inspecting the gas detection apparatus for the presence of short circuits.

According to a first aspect, the present invention provides a gas detection apparatus comprising a gas sensor element which comprises at least one sensor cell including a solid electrolyte member and a pair of electrodes provided on opposite sides of the solid electrolyte member, and a plurality of external connection terminals electrically connected to the electrodes of the sensor cell; and a gas-sensor control circuit for controlling the gas sensor element, the gas-sensor control circuit comprising a plurality of control terminals electrically connected to respective external connection terminals of the gas sensor element, an inspection current supply circuit for supplying an inspection current to an inspected terminal, which is a control terminal to be inspected for presence or absence of a short circuit to a predetermined potential, an inspection potential measurement circuit for measuring the potential of the inspected terminal, and an uninspected terminal impedance increasing circuit for increasing the impedance of the gas-sensor control circuit as viewed from an uninspected terminal, which is a control terminal other than the inspected terminal.

The gas inspection apparatus of the present invention includes an uninspected terminal impedance increasing circuit for increasing the impedance of the gas-sensor control circuit as viewed from an uninspected terminal. When the impedance of the gas-sensor control circuit as viewed from the uninspected terminal is made high by means of the uninspected terminal impedance increasing circuit, the gas sensor element can be electrically cut off from a circuit portion of the gas-sensor control circuit, the circuit portion being connected to the uninspected terminal. The short-circuit inspection is performed for the inspected terminal in this state. Therefore, even when the inspected terminal, or a wiring line or the like connected thereto (hereinafter also referred to as "inspected terminal" or the like) is short-circuited to a predetermined potential, such as to the power-source or ground potential, or when an inspection current is supplied from the inspection current supply circuit, the gas sensor element is not adversely affected. Such an adverse effect can occur when a current flows from the uninspected terminal of the gas-sensor control circuit to a short-circuited portion or the inspected terminal via the sensor cell, or when current flows, in the opposite direction, from the short-circuited portion or the inspected terminal to the uninspected terminal of the gas-sensor control circuit via the sensor cell, with the result that current flows through the sensor cell excessively or in an improper direction. Thus, the gas detection apparatus of the present invention can perform short-circuit inspection, while preventing damage or other adverse influence on the gas sensor element.

If the inspected terminal or the like is short-circuited to the predetermined potential, irrespective of the supply of inspection current, the potential of the inspected terminal is maintained at the predetermined potential such as the power-source potential or the ground potential.

Meanwhile, if the inspected terminal or the like is not short-circuited to the power-source potential or the like and the gas detection apparatus is normal, the uninspected terminal; i.e., the control terminal other than the inspected terminal, is electrically cut off by means of the uninspected terminal impedance increasing circuit. Therefore, even when the inspection current is supplied to the inspected terminal, the flow of current stops when a parasitic capacitor of the inspected terminal or the like or a capacitor connected to the inspected terminal or the like is charged by the inspection current. Accordingly, within a relatively short period of time, the potential of the inspected terminal reaches a potential (e.g., the highest potential or the lowest potential that a current source can generate), which is determined depending on the characteristics of a power source (current source or the like) for supplying the inspection current. Therefore, it is possible to determine, on the basis of the potential of the inspected terminal measured by the inspection potential measurement circuit, whether the inspected terminal or the like is short-circuited to a predetermined potential or not (normal state).

The predetermined potential is a potential of a certain member to which the inspected terminal, or a wiring line or an external connection terminal of the sensor cell connected thereto, may be short-circuited, for example, through contact. Specific examples of the predetermined potential include a ground potential and a power-source (battery) potential. A potential to which the inspected terminal is highly likely to be short-circuited is selected in consideration of the shapes of the gas sensor element and the gas-sensor control circuit, the positional relationship between the inspected terminal and wiring lines connecting the element and the circuit, and the positional relationship between the certain member and the inspected terminal or the like.

The inspection potential measurement circuit may be configured to perform an inspection for a single potential; e.g., an inspection for determining whether or not the inspected terminal is short-circuited to ground potential (hereinafter also referred to as "ground short-circuit inspection") or an inspection for determining whether or not the inspected terminal is short-circuited to the power-source (hereinafter also referred to as "power-source short-circuit inspection"), or may be configured to perform the ground short-circuit inspection and the power-source short-circuit inspection simultaneously or successively.

The gas sensor element may be of any type, insofar as the gas sensor element includes at least one sensor cell and a plurality of external connection terminals electrically connected to respective electrodes of the sensor cell. Specific examples of the gas sensor element include a one-cell-type gas sensor element which includes a single sensor cell and two external connection terminals electrically connected to a pair of electrodes sandwiching the sensor cell, and a two-cell-type gas sensor element which includes two sensor cells layered together and each including paired electrodes formed on the upper and lower surfaces thereof, and three external connection terminals which are electrically connected to an electrode on the uppermost surface, an electrode on the lowermost surface, and electrodes on the inner surfaces, respectively.

Examples of gas detection apparatuses to which the present invention can be applied include not only an oxygen sensor apparatus for detecting the concentration of oxygen contained in a measured gas, but also a CO sensor apparatus, an $NO_x$ sensor apparatus, and an organic fuel gas sensor apparatus.

The uninspected terminal impedance increasing circuit may be freely configured insofar as the configured circuit can increase the impedance of the gas-sensor control circuit to a high value as viewed from the uninspected terminal. For example, the uninspected terminal impedance increasing circuit may be configured as follows. For a plurality of circuit portions of the gas-sensor control circuit, the circuit portions having output circuits whose output terminals are connected to the uninspected terminal, a known three-state output circuit is provided as each of the output circuits, or a semiconductor switch or a relay element (hereinafter also referred to as a "switching element") is interposed between the output terminals of the output circuits and the uninspected terminal. Alternatively, a switching element may be provided which electrically cuts off the uninspected terminal from the entire circuit portion of the gas-sensor control circuit, which portion is connected to the uninspected terminal.

The inspection current supply circuit is a circuit for supplying an inspection current to the inspected terminal. Examples of the inspection current supply circuit include a constant current source for generating an output current of a predetermined magnitude, a pull-up circuit which is connected to the power-source potential (e.g., battery potential) via a resistor, a pull-down circuit which is connected to ground via a resistor, and a resistor division circuit (voltage divider) which divides the potential difference between the power-source potential and the ground potential to provide a desired potential. The direction of inspection current supplied to the inspected terminal is determined in consideration of the predetermined potential to which the inspected terminal may be short-circuited. The inspection current may flow from the inspection current supply circuit toward the gas sensor element via the inspected terminal, or flow in a reverse direction.

When the inspected terminal or the like is short-circuited to the power-source or ground potential, a large short circuit current may flow through the inspection current supply circuit and the inspected terminal. The inspection current supply circuit is desirably configured to limit the current flowing through the inspection current supply circuit.

When the inspection current is supplied to the inspected terminal, the inspected terminal assumes a different potential depending on whether or not the inspected terminal or the like is short-circuited. Accordingly, the inspection potential measurement circuit may be freely configured insofar as it enables the circuit to distinguish these different potentials from one another. Therefore, the inspection potential measurement circuit may be a circuit which is configured to obtain the potential of the inspected terminal as an analog value or a digital value, as in the case of an electrometer (voltmeter), or a potential comparator for comparing the potential of the inspected terminal with a preset potential.

In the gas detection apparatus, preferably, the gas sensor element includes a detection cell and a pump cell as the sensor cell, and first through third external connection terminals as the external connection terminals; a measurement chamber in communication with a measured space is formed between the detection cell and the pump cell; the detection cell includes a first detection electrode facing the measurement chamber and a second detection electrode facing the first detection electrode via a solid electrolyte member, and generates a cell electromotive force in accordance with the oxygen concentration within the measurement chamber; the pump cell includes a first pump electrode facing the measurement chamber and a second pump electrode facing the first pump electrode via a solid electrolyte member, and pumps oxygen out of the measurement chamber or pumps oxygen into the measurement chamber in accordance with current supplied thereto; of the external connection terminals, the first external connection terminal is electrically connected to the second detection electrode, the second external connection terminal is electrically connected to the first detection electrode and the first pump electrode electrically connected to one another, and the third external connection terminal is electrically connected to the second pump electrode; and the inspected terminal of the gas-sensor control circuit is electrically connected to the first external connection terminal, and first and second uninspected terminals are electrically connected to the second and third external connection terminals, respectively.

In a gas detection apparatus using a so-called two-cell-type gas sensor element; i.e., a gas sensor element including a pump cell and a detection cell, the gas-sensor control circuit supplies current between the second external connection terminal connected to the first pump electrode of the pump cell and the third external connection terminal connected to the second pump electrode of the pump cell, to thereby pump oxygen out of or into the measurement chamber. Meanwhile, the first detection electrode of the detection cell is electrically connected to the second external connection terminal, and the second detection electrode of the detection cell is electrically connected to the first external connection terminal.

The following considers a situation in which the first external connection terminal, or a wiring line or the second detection electrode connected thereto is short-circuited to the power-source potential or the ground potential. When the gas detection apparatus is started in this state so as to supply current to the pump cell, in some cases, current flows excessively, or in an improper direction, from a power source, which supplies current to the pump cell, to the short-circuited first external connection terminal or the like via the detection cell. Alternatively, current flows excessively, or in an improper direction, from the short-circuited first external connection terminal or the like to the gas-sensor control circuit via the detection cell. In such a case, the solid electrolyte member which constitutes the detection cell may suffer blackening.

In order to prevent a failure of the gas sensor element, such as a rupture thereof stemming from current which flows excessively or in an improper direction because of a short circuit, a measure, such as immediately cutting off the power source of the gas-sensor control circuit upon detection of a short circuit of a wiring line or the like, can be taken. However, since current has already flowed excessively or in an improper direction before detection of a short circuit of a wiring line or the like, the solid electrolyte member which constitutes the detection cell is highly likely to have already suffered blackening. That is, this method cannot prevent a rupture of the detection cell or the gas sensor element with certainty.

In contrast, in the gas detection apparatus of the present invention, the gas sensor element can be electrically cut off from circuit portions of the gas-sensor control circuit, which portions are electrically connected to the first and second uninspected terminals, by increasing the impedance of the gas-sensor control circuit as viewed from the first and second uninspected terminals. Accordingly, in this state, the inspection current is supplied to the inspected terminal electrically connected to the first external connection terminal of the gas sensor element, and the potential of the inspected terminal is measured. Therefore, current does not flow through the detection cell or the pump cell excessively or in an improper direction. Accordingly, it is possible to safely inspect the inspected terminal, the first external connection terminal connected thereto, or the wiring line connected thereto so as to determine whether or not a short circuit to a predetermined potential such as the ground potential or the power-source potential has occurred, while preventing failure of the gas sensor element such as the detection cell.

A gas sensor element is known in which the second detection electrode of the detection cell is disposed in a closed space isolated from the outside, and a small, constant current is supplied to the detection cell so that the closed space functions as a reference oxygen chamber. In such a gas sensor element, when current flows though the detection cell excessively or in an improper direction because of the occurrence of a short circuit, the pressure of the reference oxygen chamber increases, and the gas sensor element may rupture. Even in such a case, the gas detection apparatus of the present invention can prevent current from flowing though the detection cell or the pump cell excessively or in an improper direction, so that the gas detection apparatus can perform short-circuit inspection while preventing damage to or other adverse influence on the gas sensor element.

In the gas detection apparatus according to the first aspect of the present invention, preferably, the gas-sensor control circuit includes one or more output circuits having one or more output terminals connected to the uninspected terminal or the first and second uninspected terminals; and the uninspected terminal impedance increasing circuit is an output impedance increasing circuit which increases the impedance of the respective one or more output terminals of the one or more output circuits as viewed from the uninspected terminal or the first and second uninspected terminals.

In the gas detection apparatus, the impedance increasing circuit for increasing the impedance of the gas-sensor control circuit as viewed from the uninspected terminal may be configured by providing a switching element which cuts off the uninspected terminal from the entire circuit portion of the gas-sensor control circuit, which portion is connected to the uninspected terminal. A similar configuration may be employed for the first or second uninspected terminals. When such a configuration is employed, in many cases, switching elements of large current capacity must be used. In general, switching elements of large current capacity are scarce and expensive. Further, in the case where the gas-sensor control circuit is fabricated from a monolithic IC such as a hybrid IC or an ASIC (Application-Specific Integrated Circuit), mounting of a switching element of large current capacity is difficult.

In contrast, in the gas detection apparatus of the present invention, the gas-sensor control circuit includes one or more output circuits having one or more output terminals connected to the uninspected terminal or the first and second uninspected terminals, and output impedance increasing means for increasing the impedance of the respective one or more output terminal of the one or more output circuits as viewed from the uninspected terminal or the first and second uninspected terminals. Accordingly, for each output circuit, the use of a small switching element having a relatively small current capacity which corresponds to the magnitude of current flowing through the output circuit is sufficient. Therefore, the switching element is easy to obtain and is inexpensive. Alternatively, the switching element can be fabricated from a monolithic IC such as a hybrid IC or an ASIC. Accordingly, the gas detection apparatus can be easily manufactured at low cost.

In particular, if use of a switching element having a relatively small current capacity enables fabrication of a gas-sensor control circuit from a monolithic IC such as a hybrid IC or an ASIC, a compact and inexpensive gas detection apparatus can be obtained.

Notably, the output impedance increasing circuit may be configured freely insofar as it can bring the output circuit, in response to a control signal, to an ordinary output state in which an output signal can be transmitted to the uninspected terminal or a state in which the output signal is cut off and the impedance of the output circuit as viewed from the uninspected terminal is increased to a sufficiently high level. Specific examples of the output impedance increasing circuit include an output circuit using a known three-state output circuit, an output circuit whose output-stage power can be cut off, and an output circuit to which a switching transistor is connected.

In the gas detection apparatus according to the first aspect of the present invention, preferably, the gas-sensor control circuit includes an inspected terminal impedance increasing circuit which increases the impedance of the gas-sensor control circuit as viewed from the inspected terminal.

In this case, the impedance of the gas-sensor control circuit as viewed from the inspected terminal can be made high. Therefore, when the inspected terminal is determined to be short-circuited to the predetermined potential, the gas sensor element can be electrically isolated from the gas-sensor control circuit by use of not only the uninspected terminal impedance increasing circuit but also the inspected terminal impedance increasing circuit. This prevents the gas sensor element from being damaged or adversely influenced by current from, for example, a current source contained in the gas-sensor control circuit before a measure against the short circuit, such as removal of the cause of the short circuit, is taken. The gas sensor element is thus released from the short-circuited state.

According to a second aspect, the present invention provides a gas-sensor control circuit for controlling a gas sensor element which comprises at least one sensor cell including a solid electrolyte member and a pair of electrodes provided on opposite sides of the solid electrolyte member, and a plurality of external connection terminals electrically connected to the electrodes of the sensor cell. The gas-sensor control circuit comprises a plurality of control terminals electrically connected to respective external connection terminals of the gas sensor element, an inspection current supply circuit for supplying an inspection current to an inspected terminal, which is a control terminal to be inspected for presence or absence of a short circuit to a predetermined potential, an inspection potential measurement circuit for measuring the potential of the inspected terminal, and an uninspected terminal impedance increasing circuit for increasing the impedance of the gas-sensor control circuit as viewed from an uninspected terminal, which is a control terminal other than the inspected terminal.

The gas-sensor control circuit of the present invention includes an uninspected terminal impedance increasing circuit for increasing the impedance of the gas-sensor control circuit as viewed from an uninspected terminal. When the inspected terminal is inspected for a short circuit in a state in which the impedance of the gas-sensor control circuit as viewed from the uninspected terminal is made high, excessive current or a damaging reverse current does not flow through the uninspected terminal or the sensor cell connected thereto, even when the inspected terminal or the like is short-circuited to the predetermined potential, or when an inspection current is supplied to the inspected terminal. Accordingly, the gas-sensor control circuit of the present invention enables safe performance of the short-circuit inspection while preventing a rupture or deterioration in measurement characteristics of the gas sensor element even when the inspected terminal or the like is short-circuited to the predetermined potential.

In the gas-sensor control circuit according to the second aspect of the present invention, preferably, the gas sensor element includes a detection cell and a pump cell as the sensor cell, and first through third external connection terminals as the external connection terminals; a measurement chamber in communication with a measured space is formed between the detection cell and the pump cell; the detection cell includes a first detection electrode facing the measurement chamber and a second detection electrode facing the first detection electrode via a solid electrolyte member, and generates a cell electromotive force in accordance with the oxygen concentration within the measurement chamber; the pump cell includes a first pump electrode facing the measurement chamber and a second pump electrode facing the first pump electrode via a solid electrolyte member, and pumps oxygen out of the measurement chamber or pumps oxygen into the measurement chamber in accordance with current supplied thereto; of the external connection terminals, the first external connection terminal is electrically connected to the second detection electrode, the second external connection terminal, the first detection electrode and the first pump electrode are electrically connected to one another, and the third external connection terminal is electrically connected to the second pump electrode; and the inspected terminal is electrically connected to the first external connection terminal of the gas sensor element, and first and second uninspected terminals are electrically connected to the second and third external connection terminals, respectively.

In the gas-sensor control circuit of the present invention, it is possible to supply an inspection current to the inspected terminal electrically connected to the first external connection terminal of the gas sensor element and to measure the potential of the inspected terminal, in a state in which the impedance of the gas-sensor control circuit as viewed from the first and second uninspected terminals is made high by the uninspected terminal impedance increasing circuit. Therefore, even when the inspected terminal or the like is short-circuited to a predetermined potential, excessive current or current of an improper (reverse) direction does not flow between the inspected terminal and the first or second uninspected terminals of the gas-sensor control circuit. Accordingly, the detection cell or the pump cell is connected between these terminals. Thus, the gas-sensor control circuit of the present invention enables safe short-circuit inspection while preventing a rupture or deterioration in measured characteristics of the detection cell or the pump cell even when the inspected terminal or the like is short-circuited to the predetermined potential or the like.

In the gas-sensor control circuit according to the second aspect of the present invention, preferably, the gas-sensor control circuit includes one or more output circuits having one or more output terminals connected to the uninspected terminal or the first and second uninspected terminals; and the uninspected terminal impedance increasing circuit is an output impedance increasing circuit which increases the impedance of the respective one or more output terminals of the one or more output circuits as viewed from the uninspected terminal or the first and second uninspected terminals.

The gas-sensor control circuit of the present invention includes one or more output circuits having one or more output terminals connected to the uninspected terminal or the first and second uninspected terminals, and an output impedance increasing circuit for increasing the impedance of the respective one or more output terminals of the one or more output circuits as viewed from the uninspected terminal or the first and second uninspected terminals. Accordingly, the output impedance increasing circuit can be formed by use of inexpensive switching elements having a small current capacity, and thus, the gas-sensor control circuit can be manufactured at low cost.

In particular, when the gas-sensor control circuit, including the output impedance increasing circuit, is fabricated by use of a monolithic IC such as a hybrid IC or an ASIC, a compact and inexpensive gas detection apparatus can be obtained.

Preferably, the gas-sensor control circuit according to the second aspect of the present invention includes an inspected terminal impedance increasing circuit which increases the impedance of the gas-sensor control circuit as viewed from the inspected terminal.

In this case, the impedance of the gas-sensor control circuit as viewed from the inspected terminal can be made high. Therefore, when the inspected terminal is determined to be short-circuited to the predetermined potential, the gas sensor element can be electrically cut off from the gas-sensor control circuit by use of not only the uninspected terminal impedance increasing circuit but also the inspected terminal impedance increasing circuit. This prevents the gas sensor element from being adversely influenced by current from, for example, a current source contained in the gas-sensor control circuit, during a period before a measure is taken against a short circuit, such as removal of the cause of the short circuit. The gas sensor element is thereby released from the short circuited state.

According to a third another aspect, the present invention provides a method for inspecting a gas detection apparatus which includes a gas sensor element which comprises at least one sensor cell including a solid electrolyte member and a pair of electrodes provided on opposite sides of the solid electrolyte member, and a plurality of external connection terminals electrically connected to the electrodes of the sensor cell; and a gas-sensor control circuit for controlling the gas sensor element, the gas-sensor control circuit comprising a plurality of control terminals electrically connected to respective external connection terminals of the gas sensor element, an inspection current supply circuit for supplying an inspection current to an inspected terminal, which is a control terminal to be inspected for presence or absence of a short circuit to a predetermined potential, an inspection potential measurement circuit for measuring the potential of the inspected terminal, and an uninspected terminal impedance increasing circuit for increasing the impedance of the gas-sensor control circuit as viewed from an uninspected terminal, which is a control terminal other than the inspected terminal. The method comprises an uninspected terminal impedance increasing step of increasing the impedance of the gas-sensor control circuit as viewed from the uninspected terminal by means of the uninspected terminal impedance increasing circuit; an inspection current supply step of supplying an inspection current to the inspected terminal by means of the inspection current supply circuit; and a diagnosis step of determining, on the basis of the potential of the inspected terminal, whether or not the inspected terminal is short-circuited to the predetermined potential.

In the method for inspecting a gas inspection apparatus according to the present invention, in a state in which the impedance of the gas-sensor control circuit as viewed from the uninspected terminal is made high (i.e., in a state in which the gas sensor element is electrically cut off from the uninspected terminal and a circuit portion of the gas-sensor control circuit, the circuit portion being connected to the uninspected terminal), a current is supplied to the inspected terminal. A determination is then made as to whether or not the inspected terminal is short-circuited to the predetermined potential on the basis of the potential of the inspected terminal. By virtue of this method, even when the inspected terminal, or a wiring line or the like connected thereto is short-circuited to the predetermined potential, or when an inspection current is supplied from the inspection current supply circuit to the inspected terminal, no current flows to the uninspected terminal or the sensor cell connected thereto. As such, neither excessive current nor current of an improper (reverse) direction flows to the sensor cell. Therefore, failures, such as deterioration in measurement characteristics, hardly occur, which failures would otherwise occur due to blackening of the solid electrolyte member constituting the gas sensor element. Thus, the inspected terminal of the gas detection apparatus can be safely inspected for short circuits.

In the diagnosis step, any diagnosis method can be employed insofar as the diagnosis method can distinguish the case where the inspected terminal is not short-circuited (normal) and the case where the inspected terminal is short-circuited (failure). Examples of the diagnosis method include a method of measuring the potential of the inspected terminal after waiting a predetermined period of time after the start of supply of the inspection current, and determining on the basis of the potential level whether or not the inspected terminal is short-circuited; and a method of monitoring the potential of the inspected terminal while supplying the inspection current, and determining on the basis of a manner of change in potential whether or not the inspected terminal is short-circuited.

In the inspection method for a gas detection apparatus according to the third aspect of the present invention, preferably, the diagnosis step includes a waiting step of waiting a predetermined period of time after the start of supply of the inspection current; and a short-circuit determination step of determining, after elapse of the predetermined period of time, whether or not the inspected terminal is short-circuited to the predetermined potential, on the basis of the potential of the inspected terminal.

In some cases, a capacitor is connected to the inspected terminal in order to cope with noise. In such a case, even when the inspection current is supplied to the inspected terminal, the potential of the inspected terminal changes only gradually with charging of the capacitor. In particular, in the case where the magnitude of the inspection current is made smaller in consideration of the consumed current (consumed power), the potential of the inspected terminal changes only slightly even when the capacitor is charged (or discharged) by the inspection current for a short period of time.

In view of the above, in the method for inspecting a gas detection apparatus according to the present invention, upon elapse of the predetermined period of time after start of supply of current to the inspected terminal by the inspection current supply circuit, determination as to whether or not the inspected terminal is short-circuited to the predetermined potential is performed on the basis of the potential of the inspected terminal. Therefore, even in the case where the potential of the inspected terminal changes gradually, the determination as to whether or not the inspected terminal is short-circuited to the predetermined potential can be performed without fail.

In the short-circuit determination step, any determination method can be employed insofar as the method can distinguish, after elapse of the predetermined period of time, the potential of the inspected terminal in the case where the inspected terminal is not short-circuited from the potential of the inspected terminal in the case where the inspected terminal is short-circuited. In an example method, a comparator is used so as to determine whether the potential of the inspected terminal is higher or lower than a threshold value corresponding to the mid value between a potential which the inspected terminal is predicted to assume when the inspected terminal is short-circuited to the predetermined potential and a potential which the inspected terminal is predicted to assume when the inspected terminal is not short-circuited.

In the method for inspecting a gas detection apparatus according to the third aspect of the present invention, preferably, the short-circuit determination step determines that the inspected terminal is short-circuited to the predetermined potential when the inspected terminal assumes a potential between a threshold potential and the predetermined potential after elapse of the predetermined period of time.

In the short-circuit determination step of the inspection method, determination as to whether or not the inspected terminal is short-circuited to the predetermined potential is performed by comparing the potential of the inspected terminal and the threshold potential. In this case, the determination as to whether a short circuit is present or not can be easily performed through a single comparison operation.

Any comparison means can be used to compare the potential of the inspected terminal and the threshold potential. Examples of the comparison means include a comparator which directly compares the potential of the inspected terminal and the threshold potential, and means for converting an analog value representing the potential of the inspected terminal to a digital value and comparing the digital value with a value representing the threshold potential.

According to a fourth aspect, the present invention provides a method for inspecting a gas detection apparatus which includes a gas sensor element which comprises at least one sensor cell including a solid electrolyte member and a pair of electrodes provided on opposite sides of the solid electrolyte member, and a plurality of external connection terminals electrically connected to the electrodes of the sensor cell; and a gas-sensor control circuit for controlling the gas sensor element, the gas-sensor control circuit comprising a plurality of control terminals electrically connected to respective external connection terminals of the gas sensor element; a first inspection current supply circuit for supplying to an inspected terminal a first inspection current flowing in a first direction, the inspected terminal being a control terminal to be inspected for presence or absence of a short circuit to first and second predetermined potentials; a second inspection current supply circuit for supplying to the inspected terminal a second inspection current flowing in a second direction opposite the first direction; an inspection potential measurement circuit for measuring the potential of the inspected terminal; and an uninspected terminal impedance increasing circuit for increasing the impedance of the gas-sensor control circuit as viewed from an uninspected terminal, which is a control terminal other than the inspected terminal. The method comprises an uninspected terminal impedance increasing step of increasing the impedance of the gas-sensor control circuit as viewed from the uninspected terminal by means of the uninspected terminal impedance increasing circuit; a first inspection current supply step of supplying the first inspection current to the inspected terminal by means of the first inspection current supply circuit; a first diagnosis step of determining, on the basis of the potential of the inspected terminal to which the first inspection current has been supplied, whether or not the inspected terminal is short-circuited to the first predetermined potential; a second inspection current supply step of supplying the second inspection current to the inspected terminal by means of the second inspection current supply circuit; and a second diagnosis step of determining, on the basis of the potential of the inspected terminal to which the second inspection current has been supplied, whether or not the inspected terminal is short-circuited to the second predetermined potential.

In the inspection apparatus for a gas detection apparatus according to the fourth aspect of the present invention, inspection currents of first and second directions are supplied to the inspected terminal, and the inspected terminal is inspected for presence or absence of a short circuit to two predetermined potentials.

For example, consider that the flow direction from the inspected terminal toward the external connection terminal of the gas sensor element is the first direction, and that the flow direction opposite thereto is the second direction. Further, the first predetermined potential is taken as the ground potential, and the second predetermined potential is the power-source potential. In such a case, by the first inspection current supply step and the first diagnosis step, the wiring line or the like connected to the inspected terminal can be inspected for presence or absence of a short circuit to the ground potential; and by the second inspection current supply step and the second diagnosis step, the wiring line or the like connected to the inspected terminal can be inspected for presence or absence of a short circuit to the power-source potential. As described above, in the inspection method of the present invention, inspection can be performed so as to determine short circuits to two predetermined potentials; e.g., the ground potential and the power-source potential.

Notably, the direction of the inspection current supplied from the inspection current supply circuit can be determined such that the second direction corresponds to the flow direction toward the inspected terminal, and the first direction corresponds to the flow direction opposite the second direction.

In the method for inspecting a gas detection apparatus according to the fourth aspect of the present invention, preferably, the first diagnosis step includes a first waiting step of waiting a first predetermined period of time after the start of supply of the first inspection current, and a first short-circuit determination step of determining, after elapse of the first predetermined period of time, whether or not the inspected terminal is short-circuited to the first predetermined potential, on the basis of the potential of the inspected terminal; and the second diagnosis step includes a second waiting step of waiting a second predetermined period of time after the start of supply of the second inspection current, and a second short-circuit determination step of determining, after elapse of the second predetermined period of time, whether or not the inspected terminal is short-circuited to the second predetermined potential, on the basis of the potential of the inspected terminal.

In the gas detection apparatus, in some cases, a capacitor is connected to the inspected terminal of the gas-sensor control circuit in order to cope with noise. Moreover, the magnitudes of the first and second inspection currents are made smaller in consideration of the consumed current (consumed power) in some cases. In such a case, a long time is required to charge or discharge the capacitor with the first and second inspection currents, and short-period supply of current results in only a small change in the potential of the inspected terminal, so that the determination becomes difficult in some cases.

In view of the above, in the method for inspecting a gas detection apparatus according to the fourth aspect of the present invention, in the first diagnosis step, when the first predetermined period of time elapses after start of supply of current to the inspected terminal by the first inspection current supply circuit, determination as to whether or not the inspected terminal is short-circuited to the first predetermined potential is performed on the basis of the potential of the inspected terminal. Similarly, in the second diagnosis step, when the second predetermined period of time elapses after start of supply of current to the inspected terminal by the second inspection current supply circuit, determination as to whether or not the inspected terminal is short-circuited to the second predetermined potential is performed on the basis of the potential of the inspected terminal. Therefore, even in the case where the potential of the inspected terminal changes gradually due to a capacitor connected to the inspected terminal, the determination as to whether or not the inspected terminal is short-circuited to the first or second predetermined potential is performed without fail.

In the inspection method for a gas detection apparatus according to the fourth aspect of the present invention, preferably, the first short-circuit determination step determines that the inspected terminal is short-circuited to the first predetermined potential when the inspected terminal assumes a potential between a first threshold potential and the first predetermined potential after elapse of the first predetermined period of time; and the second short-circuit determination step determines that the inspected terminal is short-circuited to the second predetermined potential when the inspected terminal assumes a potential between a second threshold potential and the second predetermined potential after elapse of the second predetermined period of time, wherein the second threshold potential is between the first threshold potential and the second predetermined potential.

According to the inspection method for a gas detection apparatus, in the first short-circuit determination step, determination as to whether the inspected terminal is short-circuited to the first predetermined potential or not is performed by comparing the potential of the inspected terminal and the first threshold potential; and in the second short-circuit determination step, determination as to whether or not the inspected terminal is short-circuited to the second predetermined potential is performed by comparing the potential of the inspected terminal and the second threshold potential. In this case, the determination as to whether or not the inspected terminal is short-circuited to the first predetermined potential and the determination as to whether or not the inspected terminal is short-circuited to the second predetermined potential can be performed by a simple method.

In the method for inspecting a gas detection apparatus according to the fourth aspect of the present invention, preferably, the inspection current supply circuit supplies an inspection current to the inspected terminal such that the potential of the inspected terminal becomes equal to a predetermined intermediate potential between the first and second predetermined potentials when the inspected terminal is not short-circuited to either of the first predetermined potential or the second predetermined potential; and the diagnosis step comprises a waiting step of waiting a predetermined period of time after the start of supply of the inspection current, and a short-circuit determination step of determining, after elapse of the predetermined period of time, whether the inspected terminal is short-circuited to the first predetermined potential or the second predetermined potential on the basis of the potential of the inspected terminal.

In the above method for inspecting a gas detection apparatus, the inspection current is supplied to the inspected terminal by use of the above-described inspection current supply circuit. Accordingly, after elapse of the predetermined period of time, the inspected terminal assumes a potential close to the predetermined intermediate potential when the inspected terminal is not short-circuited to either of the first predetermined potential or the second predetermined potential. When the inspected terminal is short-circuited to the first predetermined potential, the inspected terminal assumes a potential equal to or close to the first predetermined potential. When the inspected terminal is short-circuited to the second predetermined potential, the inspected terminal assumes a potential equal to or close to the second predetermined potential. Accordingly, when the measured potential of the inspected terminal after elapse of the predetermined period of time is employed, the presence or absence of a short circuit to the first predetermined potential or the second predetermined potential can be determined easily and quickly by use of a single type of inspection current.

The inspection current supply circuit of the present invention may have any configuration insofar as it can supply an inspection current which brings the potential of the inspected terminal to the predetermined intermediate potential when the inspected terminal is not short-circuited to either of the first predetermined potential the second predetermined potential. Examples of the inspection current supply circuit include a pull-up-down circuit which divides the potential difference between the power-source potential and the ground potential by use of resistors (voltage divider circuit), and a constant current circuit whose output potential becomes equal to the predetermined intermediate potential when no current flows therethrough.

Preferably, the short-circuit determination step determines that the inspected terminal is short-circuited to the first predetermined potential when the inspected terminal assumes a potential between a first threshold potential and the first predetermined potential after elapse of the predetermined period of time, and determines that the inspected terminal is short-circuited to the second predetermined potential when the inspected terminal assumes a potential between a second threshold potential and the second predetermined potential after elapse of the predetermined period of time, wherein the second threshold potential is between the first threshold potential and the second predetermined potential.

In this case, determination as to whether or not the inspected terminal is short-circuited to the first or second predetermined potential is performed by comparing the potential of the inspected terminal and the first and second threshold potentials. Therefore, the short-circuit determination can be easily performed.

In the inspection methods according to the present invention, preferably, the gas-sensor control circuit includes an inspected terminal impedance increasing circuit which increases the impedance of the gas-sensor control circuit as viewed from the inspected terminal; and the inspection method further comprises an inspected terminal impedance increasing step of increasing the impedance of the gas-sensor control circuit as viewed from the inspected terminal when it is determined that the inspected terminal is short-circuited to the predetermined potential or the first or second predetermined potential.

In the inspection methods of the present invention, when the inspected terminal is determined to be short-circuited to the predetermined potential or the first or second predetermined potential (hereinafter referred to as the "predetermined potential, etc."), as in the case of the uninspected terminal, the impedance of the gas-sensor control circuit as viewed from the inspected terminal is made high. That is, when the inspected terminal is determined to be short-circuited to the predetermined potential, etc., the gas sensor element is electrically cut off from the gas-sensor control circuit. By virtue of this, it is possible to prevent the gas sensor element from being adversely influenced by current from, for example, a current source contained in the gas-sensor control circuit, during a period between a point in time when a short circuit is found through inspection and a point in time when a measure is taken against the short circuit, such as removal of the cause of the short circuit. The gas sensor element is thereby released from the short circuited state.

In the inspection methods according to the present invention, preferably, the uninspected terminal impedance increasing step is performed immediately after the power to the gas-sensor control circuit is turned on.

In the inspection methods of the invention, preferably, the uninspected terminal impedance increasing step is performed immediately after power to the gas-sensor control circuit is turned on. Therefore, when the inspected terminal is determined to be short-circuited to the predetermined potential, etc., and without excessive current or current of an improper (reverse) direction having been supplied to the gas sensor element, a control measure against the short circuit is taken, such as stopping operation of the gas detection apparatus or cutting off the power source. An adverse effect of the short circuit on the gas sensor element, such as a rupture or deterioration in measurement characteristics of the gas sensor element, can thereby be prevented with certainty.

BRIEF DESCRIPTION OF THE DRAWINGS

Various objects, features and attendant advantages of the present invention will be readily appreciated by reference to the following detailed description of the preferred embodiments when considered in connection with the accompanying drawings, in which.

DESCRIPTION OF THE PREFERRED EMBODIMENTS

Embodiments of the present invention will next be described with reference to the drawings. However, the present invention should not be construed as being limited thereto.

First Embodiment

A gas detection system 1 according to a first embodiment of the present invention will be described with reference to FIGS. 1 to 7.

Figure 1:
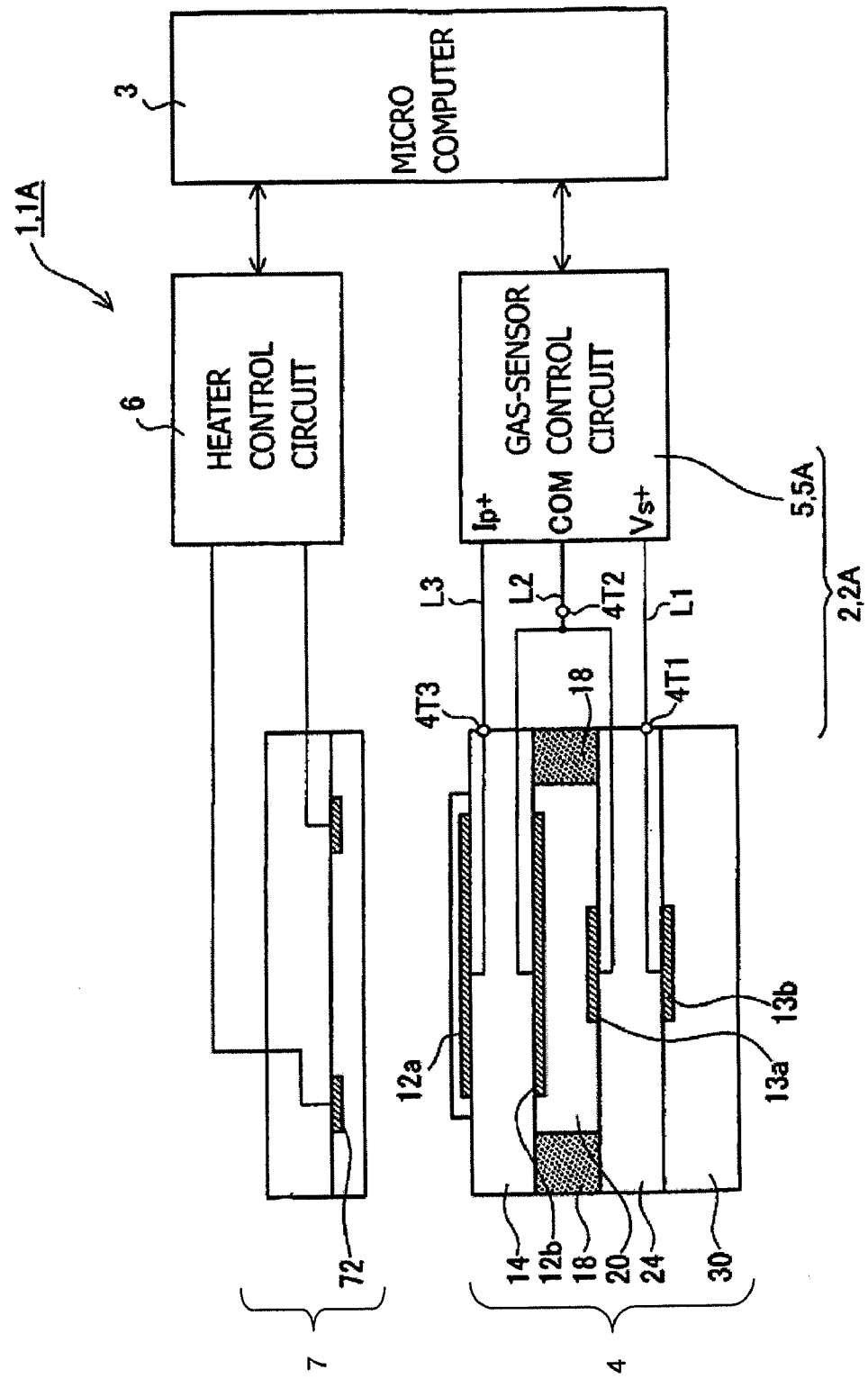
FIG. 1 is a block diagram of a gas detection system according to first and second embodiments.

As shown in FIG. 1, the gas detection system 1 of the first embodiment for measuring air-fuel ratio based on the measured concentration of oxygen in exhaust gas includes a gas detection apparatus 2 composed of a gas sensor element 4 and a gas-sensor control circuit 5; a heater 7 for maintaining the gas sensor element 4 at an operation temperature; a heater control circuit 6 for controlling the heater 7; and a microcomputer 3 for controlling the gas detection apparatus 2 and the heater control circuit 6.

Although not illustrated in the drawings, the microcomputer 3 includes a CPU (central processing unit), RAM and ROM for storing data, programs, etc., and input and output ports for receiving signals from an external circuit and for outputting signals to the external circuit. In the microcomputer 3, in accordance with programs stored in the RAM or the like, the CPU executes instructions for computation, data transfer, etc. In the microcomputer 3, signals input to the input port are reflected on the contents of an input port register, and the contents of an output port register are output to the output port as signals.

The heater 7, which is controlled by means of the heater control circuit 6, is bonded to the gas sensor element 4 via an unillustrated ceramic bonding material. The heater 7 is formed of a ceramic which predominantly contains alumina, and a heater wire 72 is buried within the ceramic. The heater control circuit 6 controls the heater 7 such that the gas sensor element 4 is maintained at 550° C. to 900° C.

The gas sensor element 4 is disposed in an exhaust gas system of a gasoline engine. The gas sensor element 4 includes two sensor cells (a pump cell 14 and a detection cell 24) bonded together, and has three element terminals 4T1, 4T2, and 4T3, which are connected to control terminals Vs+, COM, and Ip+, respectively, of the gas-sensor control circuit 5 via wiring lines L1, L2, and L3.

The gas sensor element 4 is fabricated through integral firing and includes the pump cell 14, a porous diffusion layer 18, a detection cell 24, and a reinforcement plate 30, which are layered in this order.

The pump cell 14 is formed into a thin plate-like shape from zirconia, which is an oxygen-ion conductive solid electrolyte. Porous first and second pump electrodes 12a and 12b formed of platinum are formed on opposite surfaces of the pump cell 14. The first pump electrode 12a is connected to the third control terminal Ip+ of the gas-sensor control circuit 5 via the third element terminal 4T3 and the wiring line L3, and the second pump electrode 12b is connected to the second control terminal COM of the gas-sensor control circuit 5 via the second element terminal 4T2 and the wiring line L2.

Similarly, the detection cell 24 is formed into a thin plate-like shape from zirconia, and porous first and second detection electrodes 13a and 13b formed of platinum are formed on the opposite surfaces of the detection cell 24. Of the first and second detection electrodes 13a and 13b, the first detection electrode 13a is electrically connected to the second pump electrode 12b inside the gas sensor element 4, so that the first detection electrode 13a is electrically connected to the second element terminal 4T2. Accordingly, the first detection electrode 13a is also connected to the second control terminal COM of the gas-sensor control circuit 5 via the second element terminal 4T2 and the wiring line L2. Meanwhile, the second detection electrode 13b is connected to the first control terminal Vs+ of the gas-sensor control circuit 5 via the first element terminal 4T1 and the wiring line L1.

A measurement chamber 20 is formed between the pump cell 14 and the detection cell 24 and surrounded by an insulating layer of alumina. The above-mentioned porous diffusion layer 18 is formed in the insulating layer. The measurement chamber 20 communicates with a measured gas atmosphere (e.g., atmosphere on the exhaust side of the engine) via the porous diffusion layer 18. The porous diffusion layer 18 is formed of a porous sintered material having diffusion holes which restrict gas diffusion, and controls the diffusion rate of gas flowing therethrough.

Meanwhile, the reinforcement plate 30, which is formed of ceramic and has a size approximately equal to that of the detection cell 24, is disposed in such a manner that the second detection electrode 13b of the detection cell 24 is sandwiched between the detection cell 24 and the reinforcement plate 30, whereby the overall strength of the gas sensor element 4 is increased. The reinforcement plate 30 isolates the second detection electrode 13b from the outside, whereby a closed space is formed on the side where the second detection electrode 13b is provided.

When a predetermined bias current Icp is caused to flow through the detection cell 24 from the second detection electrode 13b to the first detection electrode 13a, pumping of oxygen (pumping out and pumping in of oxygen) is effected, whereby oxygen accumulates in the closed space associated with the second detection electrode 13b, at a generally constant concentration. The oxygen accumulated in the closed space associated with the second detection electrode 13b serves as a reference gas for detection of a measured gas by the gas sensor element 4.

In the gas sensor element 4, oxygen contained in the measured gas atmosphere flows and disperses into the measurement chamber 20 via the porous diffusion layer 18 in accordance with the concentration of oxygen contained in the measured gas atmosphere. The gas sensor element 4 has characteristics such that when the air-fuel ratio of gas mixture supplied to the engine is maintained at the stoichiometric air-fuel ratio, because of a difference in oxygen concentration between the measurement chamber 20 and the reference gas at the second detection electrode 13b, a potential of 450 mV is generated in the detection cell 24. Namely, a potential difference of 450 mV is generated between the first and second detection electrodes 13a and 13b.

Incidentally, when the air-fuel ratio of gas mixture supplied to the engine changes and the concentration of oxygen contained in exhaust gas changes, the concentration of oxygen within the measurement chamber 20 of the gas sensor element 4 changes. In this gas sensor element 4, by means of the gas-sensor control circuit 5 described below, the pump current Ip flowing through the pump cell 14 is controlled such that the potential difference between the first and second detection electrodes 13a and 13b is maintained at 450 mV. In other words, oxygen is pumped by the pump cell 14 such that the atmosphere within the measurement chamber 20 is maintained the same as that when the air-fuel ratio coincides with the theoretical air-fuel ratio. In the gas sensor element 4, the concentration of oxygen contained in the measured gas is measured on the basis of the pump current Ip, and thus, the air-fuel ratio is detected.

Figure 2:
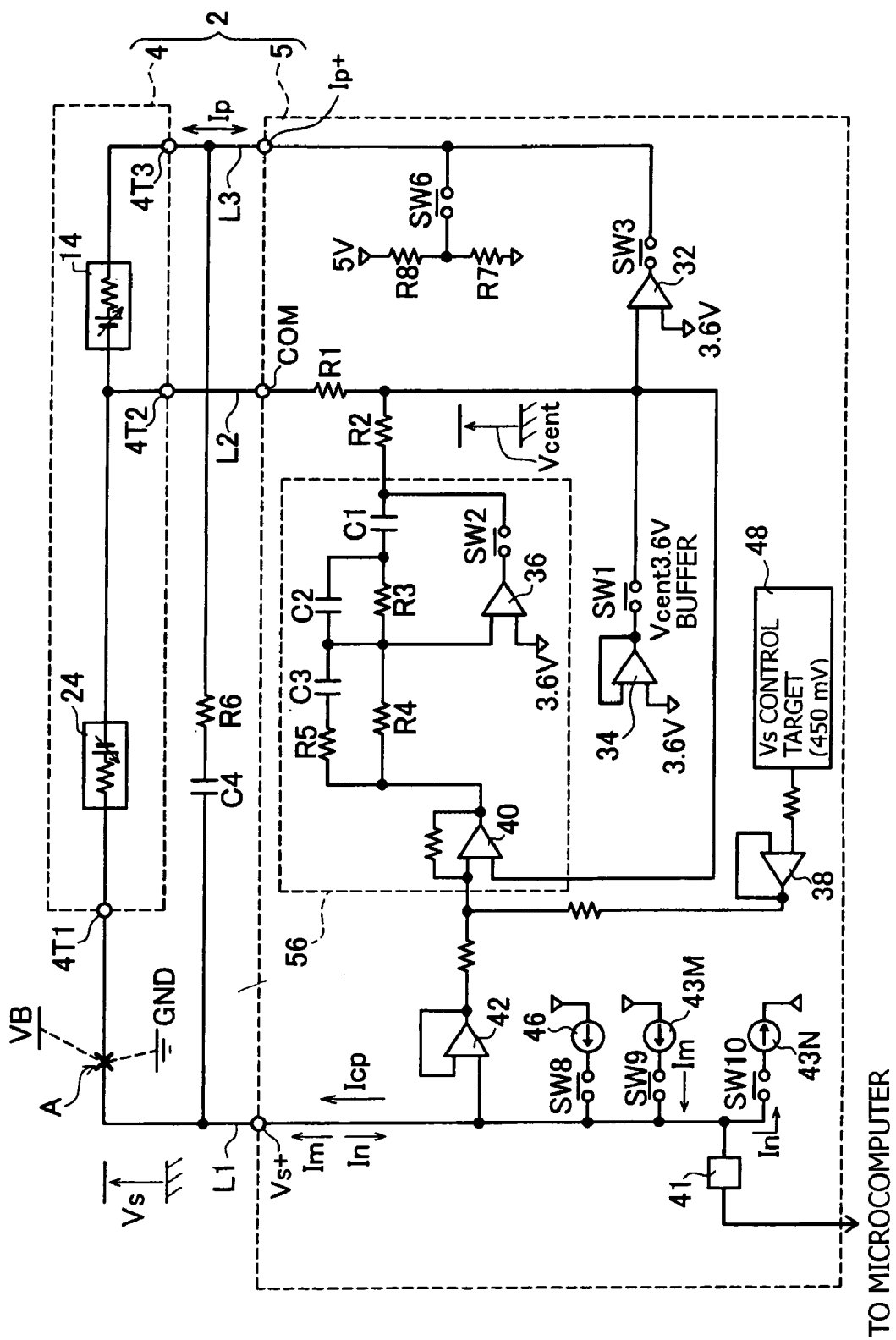
FIG. 2 is a circuit diagram showing the circuit configuration of a gas detection apparatus according to the first embodiment.

Next, the structure and operation of the gas-sensor control circuit 5 will be described with reference to FIG. 2.

The gas-sensor control circuit 5 has the above-described first through third control terminals Vs+, COM, and Ip+, which are connected to the element terminals 4T1, 4T2, and 4T3 of the gas sensor element 4 via the wiring lines L1, L2, and L3.

The gas-sensor control circuit 5 is a circuit for controlling the gas sensor element 4 and measuring the oxygen concentration of the measured gas. The gas-sensor control circuit 5 includes an operational amplifier 32 which supplies the pump current Ip for driving the pump cell 14; a PID control circuit 56 (proportional-integral-derivative controller) which improves control characteristics associated with the pump current Ip; and a constant current source 46 which supplies a predetermined bias current Icp to the detection cell 24 in order to maintain the oxygen concentration of the second detection electrode 13b constant. Further, the gas-sensor control circuit 5 includes a constant voltage source 48 which supplies a control target potential (450 mV) used for controlling the pump current Ip; and a resistor element R2 which converts the pump current Ip flowing through the pump cell 14 to a voltage signal. Moreover, the gas-sensor control circuit 5 includes switches SW1 to SW3, SW6, and SW8 to SW10. Each of these switches SW1 to SW3, SW6, and SW8 to SW10 is formed of a transistor element, and is switched between a cut-off state and a conduction state so as to open and close a circuit connected thereto.

A series circuit composed of a capacitor C4 and a resistor element R6 is interposed between the first control terminal Vs+ and the third control terminal Ip+ for noise removal.

In the gas-sensor control circuit 5, a circuit connected to the first control terminal Vs+ will first be described. The output terminals of constant current sources 43M, 43N, and 46 are connected to the first control terminal Vs+ via the switches SW9, SW10, and SW8, respectively. Further, the input terminals of a potential monitor circuit 41 and an operational amplifier 42 are connected to the first control terminal Vs+. The potential monitor circuit 41 measures the potential of the first control terminal Vs+.

The constant current sources 43M and 43N (inspection current supply circuit) for supplying an inspection current to the first control terminal Vs+ cooperate with the potential monitor circuit 41 so as to diagnose whether the first control terminal Vs+, the wiring line L1 electrically connected to the first control terminal Vs+, or the first element terminal 4T1 electrically connected to the wiring line L1 is short-circuited to the power-source potential or the ground potential. The switches SW9 and SW10 can be switched between a cut-off state and a conduction state.

The constant current source 43M supplies a positive-direction inspection current Im which flows out of the first control terminal Vs+ (hereinafter, the direction in which inspection current flows out of the first control terminal Vs+ will be referred to as a "positive direction," and the direction opposite thereto will be referred to as a "negative direction."). Meanwhile, the constant current source 43N supplies a negative-direction inspection current In which flows in a direction opposite the flow direction of the positive-direction inspection current Im. The switches SW9 and SW10 are present between the output terminals of the constant current sources 43M and 43N and the first control terminal Vs+. By switching the switches SW9 and SW10 between the cut-off state and the conduction state, the impedance of the constant current sources 43M and 43N as viewed from the first control terminal Vs+ can be switched to a low impedance, which is approximately equal to the output impedance of the constant current sources 43M and 43N, respectively, or to a high impedance (a state equivalent to a state where the constant current sources 43M and 43N are cut off).

The constant current source 43M has an upper limit in relation to the voltage (potential) that it can generate, and can supply the positive-direction inspection current Im only up to the point where the potential of the output terminal of the constant current source 43M; i.e., the potential of the first control terminal Vs+, becomes substantially equal to the power source potential VB. Similarly, the constant current source 43N has a lower limit in relation to the voltage (potential) that it can generate, and can supply the negative-direction inspection current In only up to the point where the potential of the output terminal of the constant current source 43N; i.e. the potential of the first control terminal Vs+, becomes substantially equal to the ground potential GND.

Further, the impedance of the constant current source 46 as viewed from the first control terminal Vs+ can be switched to a low impedance or a high impedance by switching the switch SW8 between the cut-off state and the conduction state.

The constant current source 46 connected to the first control terminal Vs+ supplies a bias current Icp (17 μA) which flows through the detection cell 24 so as to maintain the oxygen concentration at the second detection electrode 13b constant.

Meanwhile, the input terminal of the operational amplifier 42 is connected directly to the first control terminal Vs+, because the input impedance of the operational amplifier 42 is always high as viewed from the first control terminal Vs+.

The potential monitor circuit 41 is also connected directly to the first control terminal Vs+, because the impedance of the potential monitor circuit 41 is always high as viewed from the first control terminal Vs+. The potential monitor circuit 41 includes a known A/D converter, and converts the potential of the first control terminal Vs+ to a digital value, which is then fed to the microcomputer 3.

Therefore, when all the switches SW8, SW9, and SW10 are turned off, the impedance of the gas-sensor control circuit 5 is high as viewed from the first control terminal Vs+. That is, in this case, the gas-sensor control circuit 5 can be seen to be electrically cut off from the first control terminal Vs+.

Next, in the gas-sensor control circuit 5, a circuit connected to the second control terminal COM will be described. The above-mentioned PID control circuit 56, the above-mentioned operational amplifier 32, and another operational amplifier 34 are connected to the second control terminal COM.

The output of the PID control circuit 56 is connected to the inverted input terminal of the operational amplifier 32 via the resistor element R2. A reference potential of 3.6 V is applied to the non-inverted input terminal of the operational amplifier 32, and the output terminal of the operational amplifier 32 is connected to the third control terminal Ip+ via the switch SW3. Thus, a negative feedback circuit for controlling the pump current Ip of the gas sensor element 4 is formed. The input terminal (inverted input terminal) of the operational amplifier 32 is connected to the second control terminal COM via a resistor element R1. Therefore, the operational amplifier 32 always exhibits high impedance as viewed from the second control terminal COM.

The PID control circuit 56 performs a PID computation for the difference ΔVs between the control target value (450 mV) and the potential Vs of the first control terminal Vs+, which is the output potential of the detection cell 24, to thereby improve the control characteristics of the negative feedback control circuit including the operational amplifier 32. The PID control circuit 56 includes operational amplifiers 36 and 40, and resistor elements R3 to R5 and capacitors C1 to C3, which determine the control characteristics of the PID control circuit 56. The output of the operational amplifier 42 is supplied to the input terminal of the PID control circuit 56 (operational amplifier 40), whereby the potential Vs of the first control terminal Vs+ is supplied to the PID control circuit 56. The output of the PID control circuit 56 is supplied to the second control terminal COM via the resistor elements R2 and R1. Further, the output terminal of the PID control circuit 56 is connected via the resistor element R2 to the inverted input terminal of the operational amplifier 32 as an internal potential Vcent.

The output of the constant voltage source 48 is input to the operational amplifier 40 via an operational amplifier 38. The constant voltage source 48 is a circuit for supplying a potential (450 mV), which serves as a control target used for controlling the pump current Ip, to the PID control circuit 56 via the operational amplifier 40.

The output of the PID control circuit 56 is turned on and off by means of the switch SW2 connected to the output terminal of the operational amplifier 36. Accordingly, the impedance of the PID control circuit 56 as viewed from the second control terminal COM can be switched between low impedance and high impedance by means of turning the output terminal of the PID control circuit 56 on and off by way of the switch SW2.

The resistor element R2 converts the pump current Ip flowing through the pump cell 14 to a voltage signal, which is generated across the resistor element R2 and is supplied to the microcomputer 3 via an unillustrated differential amplifying circuit.

The operational amplifier 34 is connected to the line of the internal potential Vcent via the switch SW1. The operational amplifier 34 supplies a predetermined potential to the second control terminal COM when the gas sensor element 4 is not activated. The impedance of the operational amplifier 34 as viewed from the second control terminal COM can be switched between low impedance and high impedance by means of switching the switch SW1.

Therefore, when both the switches SW1 and SW2 are turned off, the gas-sensor control circuit 5 assumes a high impedance as viewed from the second control terminal COM. That is, in this case, the gas-sensor control circuit 5 can be seen to be electrically cut off from the second control terminal COM.

Next, in the gas-sensor control circuit 5, a circuit connected to the third control terminal Ip+ will be described. The above-mentioned operational amplifier 32 and a pull-up-down circuit are connected to the third control terminal Ip+. The pull-up-down circuit includes resistor elements R7 and R8 and divides the potential difference between the 5 V potential and the ground potential.

The pull-up-down circuit supplies a potential of 2.5 V, which is a mean potential between the 5 V potential and the ground potential, to the third control terminal Ip+ when the gas sensor element 4 is not activated.

This pull-up-down circuit is connected to the third control terminal Ip+ via the switch SW6, and, therefore, the impedance of the pull-up-down circuit as viewed from the third control terminal Ip+ can be switched between low impedance and high impedance by means of switching the switch SW6.

The output terminal of the operational amplifier 32 is connected to the third control terminal Ip+ via the switch SW3. The impedance of the operational amplifier 32 as viewed from the third control terminal Ip+ can be switched between low impedance and high impedance by means of switching the switch SW3.

Therefore, when both the switches SW3 and SW6 are turned off, the impedance of the gas-sensor control circuit 5 is high as viewed from the third control terminal Ip+. That is, in this case, the gas-sensor control circuit 5 can be electrically cut off from the third control terminal Ip+.

In order to make the impedance of the gas-sensor control circuit 5 high as viewed from the second control terminal COM and the third control terminal Ip+, a circuit configuration may be employed in which a single switch; specifically, a single switching element, is interposed between the second control terminal COM and the outputs of the PID control circuit 56 and the operational amplifier 34. In this case as well, the impedance of the gas-sensor control circuit 5 can be made high as viewed from the second control terminal COM.

However, when such a circuit configuration is employed, switching elements to be used must have a larger current capacity as compared with the case where a large number of switches SW1, etc. are used as in the first embodiment. In general, switching elements of larger current capacity tend to be expensive and not readily available. In particular, when the gas-sensor control circuit is formed by a semiconductor integrated circuit such as an ASIC, forming switching elements having a larger current capacity may be difficult.

In contrast, in the gas-sensor control circuit 5 of the first embodiment, as described above, the switches SW1, etc. are provided between the second control terminal COM and the third control terminal Ip+ and the output terminals of the corresponding circuits. Therefore, the impedance of the gas-sensor control circuit 5 as viewed from the second control terminal COM and the third control terminal Ip+ can be made high by means of turning all the switches SW1, etc. off. In this case, a switching element having a relatively small current capacity suitable for the current capacity of a circuit to which the switching element is connected is employed as a switch. Accordingly, the gas-sensor control circuit 5 can be made with parts that are readily available and inexpensive. In addition, since switching elements of larger current capacity are not required, even when a semiconductor integrated circuit is employed, the gas-sensor control circuit 5 can be easily constituted.

Moreover, in the gas-sensor control circuit 5 of the first embodiment, the switches SW8, SW9, and SW10 are connected between the first control terminal Vs+ and the output terminals of the constant current sources 46, 43M, and 43N. Therefore, the impedance of the gas-sensor control circuit 5 as viewed from the first control terminal Vs+ can be made high by means of turning all the switches SW8, SW9, and SW10 off.

Notably, control signals for controlling the switches SW1 to SW3, SW6, and SW8 to SW10 to an on state (conduction state) and an off state (cut-off state) are output from the output port of the microcomputer 3. The output signal of the potential monitor circuit 41 and the voltage generated across the resistor element R2 are supplied to the input port of the microcomputer 3. Therefore, the microcomputer 3 can perform ON/OFF control for the switches SW1 to SW3, SW6, and SW8 to SW10 of the gas-sensor control circuit 5, and can obtain a measurement value of gas concentration and the potential of the first control terminal Vs+ output from the gas-sensor control circuit 5.

Next, a method by which the gas detection system 1 of the first embodiment detects oxygen concentration will be described.

For ordinary oxygen concentration detection, in the gas-sensor control circuit 5, the switches SW1, SW9, and SW10 are turned off, and the switches SW2, SW3, SW6, and SW8 are turned on in advance. At this time, if the measured gas is in a fuel supply excessive (rich) state, the quantity of oxygen within the measurement chamber 20 becomes less than a quantity corresponding to the stoichiometric air-fuel ratio, and the potential Vs of the first control terminal Vs+ becomes higher than the control target value (450 mV), so that a difference ΔVs is produced between the control target value and the potential Vs. The difference ΔVs undergoes PID computation performed by the PID control circuit 56, and is fed back to the operational amplifier 32. Therefore, the pump current Ip flows though the pump cell 14 so as to pump oxygen by an amount corresponding to the shortage.

Meanwhile, if the measured gas is in a fuel supply insufficient (lean) state, the quantity of oxygen within the measurement chamber 20 becomes greater than the quantity corresponding to the stoichiometric air-fuel ratio, and the potential Vs of the first control terminal Vs+ becomes lower than the control target value (450 mV). Thus, the difference ΔVs is fed back to the operational amplifier 32 in a manner similar to that described above, whereby the pump current Ip flows though the pump cell 14 so as to pump out the excessive oxygen.

In this manner, in the gas detection system 1 using the gas detection apparatus 2 of the first embodiment, the magnitude of the pump current Ip, which flows through the pump cell 14 and is controlled such that the potential Vs of the first control terminal Vs+ becomes 450 mV, is measured, whereby the concentration of oxygen contained in the measured gas can be measured. Specifically, the pump current Ip is converted to a potential representing the gas concentration by means of the resistor element R2, and the potential is output to the microcomputer 3. Ultimately, the measured oxygen concentration is used for combustion control of the engine.

Next, a method by which the gas detection system 1 of the first embodiment performs short-circuit inspection will be described with reference to FIGS. 3 to 7.

In the gas detection apparatus 2, due to improper handling or a mechanical factor such as vibration of the engine, the first control terminal Vs+, the wiring line L1, or the first element terminal 4T1 may come into contact with the power source potential VB or the ground potential GND to thereby form a short circuit. In view of this, a case will be considered hereinbelow in which, as shown in FIG. 2, the wiring line L1 is short-circuited to the power source potential VB or the ground potential GND at a point A. In this case, under the assumption that a conductive path which enables large current to flow therethrough is formed by the short circuit, the potential of the first control terminal Vs+ becomes equal to the power source potential VB or the ground potential GND. As a result, current flows through the detection cell 24 from the second control terminal COM and the third control terminal Ip+ of the gas-sensor control circuit 5 towards the point A (or in the opposite direction). Therefore, there is a possibility of blackening at the detection cell 24, and the gas sensor element 4 can rupture due to an increase in pressure within the gas sensor element 4 (the second detection electrode 13b). In particular, when the wiring line L1 is short-circuited to the ground potential GND at the point A, current flows in a direction opposite the direction of current induced by the cell electromotive force of the detection cell 24, so that blackening may occur even when current flows over a short period of time or when a very small current flows.

As described above, a method for inspecting whether the wiring line L1 is short-circuited to the power source potential VB or the ground potential GND is to monitor the potential of the first control terminal Vs+ while operating the gas detection apparatus 2. However, even when the short-circuiting of the wiring line L1 to the power source potential VB or the ground potential GND is detected by use of this method, current of an improper direction or excessive current is likely to have already flowed through the detection cell 24. Therefore, using this method it is difficult to prevent the detection cell 24 from becoming ruptured.

In contrast, in the gas-sensor control circuit 5 of the first embodiment, the impedance of the gas-sensor control circuit 5 as viewed from the second control terminal COM and the third control terminal Ip+ can be made high as described above, and the first control terminal Vs+ can be inspected in this state. Therefore, by performing this inspection immediately after power of the gas detection apparatus 2 is turned on as described below, even when the first control terminal Vs+ is short-circuited to the power source potential VB or the ground potential GND, the gas detection apparatus 2 can be inspected while preventing current from flowing through the gas sensor element 4. If a measure, such as cutting off the output of the gas-sensor control circuit 5, is taken on the basis of the inspection results, breakage or rather rupturing of the detection cell 24 can be prevented with certainty, which rupture would otherwise occur due to current flowing excessively or in an improper (reverse) direction.

In the first embodiment, first, the impedance of the gas-sensor control circuit 5 as viewed from the control terminals other than the first control terminal Vs+ for which presence/absence of a short circuit is inspected; i.e., as viewed from the second control terminal COM and the third control terminal Ip+, is made high. Subsequently, a very small inspection current is supplied to the first control terminal Vs+ from the constant current source 43M or the constant current source 43N (inspection current supply circuit).

The potential of the first control terminal Vs+ is measured by means of the potential monitor circuit 41, and the measured potential is converted to a digital signal by a known A/D converter contained in the potential monitor circuit 41. The digital signal is then read by the microcomputer 3. In the microcomputer 3, the potential of the first control terminal Vs+ represented by the digital signal is compared with a preset threshold potential so as to diagnose whether the first control terminal Vs+ is short-circuited to the ground potential GND or the power source potential VB.

Specifically, the constant current source 43M is used for inspection for determining whether the first control terminal Vs+ is short-circuited to the ground potential GND, and the constant current source 43N is used for inspection for determining whether the first control terminal Vs+ is short-circuited to the power source potential VB. Changeover between the outputs of these constant current sources 43M and 43N is performed through ON/OFF control of the switches SW9 and SW10 connected to the constant current sources 43M and 43N, respectively.

Next, the method for inspecting the first control terminal Vs+ will be described in detail. Since the gas detection system 1 of the first embodiment includes the constant current sources 43M and 43N and the switches SW9 and SW10, inspection for determining whether or not a short-circuit to the power source potential VB is present and inspection for determining whether or not a short-circuit to the ground potential GND is present can be performed for the first control terminal Vs+ (wiring line L1), and these inspections can be performed in combination. In the following, four inspection methods will be described with reference to FIGS. 3 to 6; i.e., a method in which only a short-circuit to the ground potential GND is inspected; a method in which only a short-circuit to the power source potential VB is inspected; a method in which a short-circuit to the ground potential GND is inspected and then a short-circuit to the power source potential VB is inspected; and a method in which a short-circuit to the power source potential VB is inspected and then a short-circuit to the ground potential GND is inspected.

In each of these methods, the impedance of the gas-sensor control circuit 5 as viewed from the control terminals other than the first control terminal Vs+ for which presence/absence of a short circuit is inspected; i.e., as viewed from the second control terminal COM and the third control terminal Ip+, is made high.

Further, when a short-circuit to the ground potential GND is inspected, a positive-direction inspection current Im is supplied to the first control terminal Vs+ by use of the constant current source 43M. When a short-circuit to the power source potential VB is inspected, a negative-direction inspection current In is supplied to the first control terminal Vs+ by use of the constant current source 43N.

The potential of the first control terminal Vs+ is measured by means of the potential monitor circuit 41, and the measured potential is converted to a digital signal by the A/D converter contained in the potential monitor circuit 41. The digital signal is then read by the microcomputer 3. In the microcomputer 3, the potential of the first control terminal Vs+ represented by the digital signal is compared with the preset threshold potential so as to diagnose whether the first control terminal Vs+ is short-circuited to the ground potential GND or the power source potential VB.

Changeover between the outputs of these constant current sources 43M and 43N is performed through ON/OFF control of the switches SW9 and SW10 connected to the constant current sources 43M and 43N, respectively.

INSPECTION EXAMPLE 1

Inspection for Short Circuit to the Ground Potential

Figure 3:
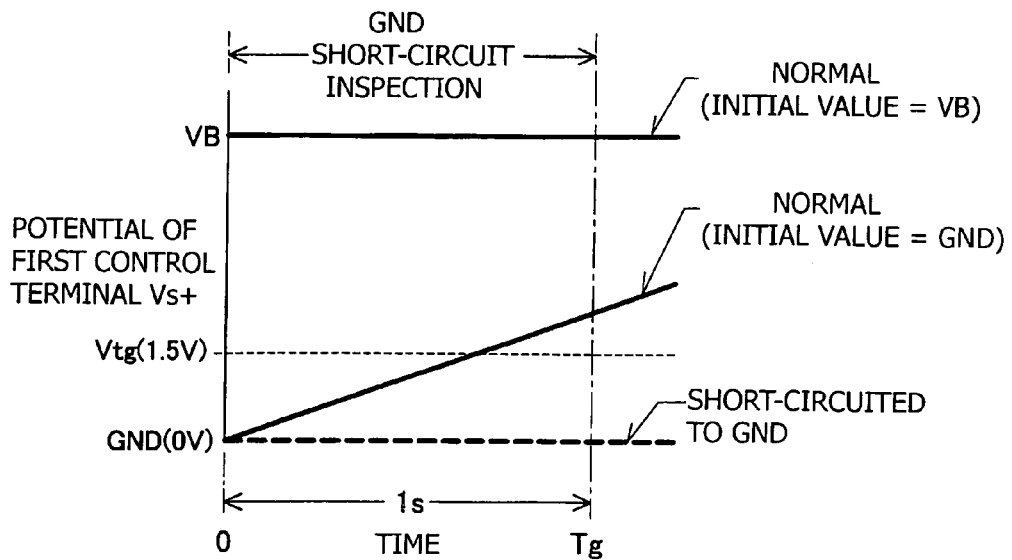
FIG. 3 is a graph showing a change in the potential of a first control terminal Vs+ of a gas-sensor control circuit obtained in Inspection Example 1 which was performed using the gas detection system of the first embodiment so as to inspect whether the first control terminal Vs+ is short-circuited to the ground potential.

FIG. 3 is a graph showing the results of an inspection in which the positive-direction inspection current Im was supplied to the first control terminal Vs+ by use of the constant current source 43M in order to determine whether or not the first control terminal Vs+ is short-circuited to the ground potential GND. The vertical direction presents potential, the horizontal direction represents time. In FIG. 3, each solid line represents the potential of the first control terminal Vs+ in a normal state; and a broken line represents a change in the potential of the first control terminal Vs+ in the case where the first control terminal Vs+ (wiring line L1) is short-circuited to the ground potential GND. Notably, in a normal state, at the time of start of inspection, the potential of the first control terminal Vs+ may assume an initial value between the power source potential VB and the ground potential GND. Therefore, the graph shows both the case where the initial value is the power source potential and the case where the initial value is the ground potential. The same applies to the graphs of FIGS. 4 to 6 to be described later.

In a normal state; i.e., when the first control terminal Vs+ (wiring line L1) is not short-circuited to the ground potential GND, if the initial value of the potential of the first control terminal Vs+ is the ground potential GND, the potential of the first control terminal Vs+ gradually increases from the ground potential GND toward the power source potential VB. At this time, since the impedance of the gas-sensor control circuit 5 as viewed from the second control terminal COM and the third control terminal Ip+ is made high, even when the constant current source 43M supplies the positive-direction inspection current Im, this current Im does not flow into the gas-sensor control circuit 5 from the second control terminal COM or the third control terminal Ip+. Accordingly, the positive-direction inspection current Im is used to charge the capacitor connected to the first control terminal Vs+, so that the potential of the first control terminal Vs+ increases gradually.

In a normal state, if the initial value of the potential of the first control terminal Vs+ is the power source potential VB, the potential of the first control terminal Vs+ is maintained at the power source potential VB and does not change, because the constant current source 43M cannot generate a voltage that is higher than the power source potential VB as described above.

In contrast, at the time of forming a short circuit; i.e., when the first control terminal Vs+ (wiring line L1) is short-circuited to the ground potential GND, irrespective of supply of the positive-direction inspection current Im, the potential of the first control terminal Vs+ is maintained at the ground potential GND or a value close to the ground potential GND. This is because the positive-direction inspection current Im flows through a conductive path formed by the short circuit.

Notably, in the first embodiment, when a short-circuit to the ground potential is inspected, the quantity of current that flows to the ground potential is limited by use of the constant current source 43M so as to prevent excess flow of current and resultant consumption of large electrical power during the short-circuit inspection.

Accordingly, inspection for determining whether or not the first control terminal Vs+ is short-circuited to the ground potential GND can be performed by determining whether the potential of the first control terminal Vs+ is higher than a ground-short-circuit threshold potential Vtg (1.5 V in the first embodiment), when a predetermined period of time Tg (1 second in the present example) has elapsed after start of supply of the positive-direction inspection current Im to the first control terminal Vs+.

INSPECTION EXAMPLE 2

Inspection for Short Circuit to the Power Source Potential

Figure 4:
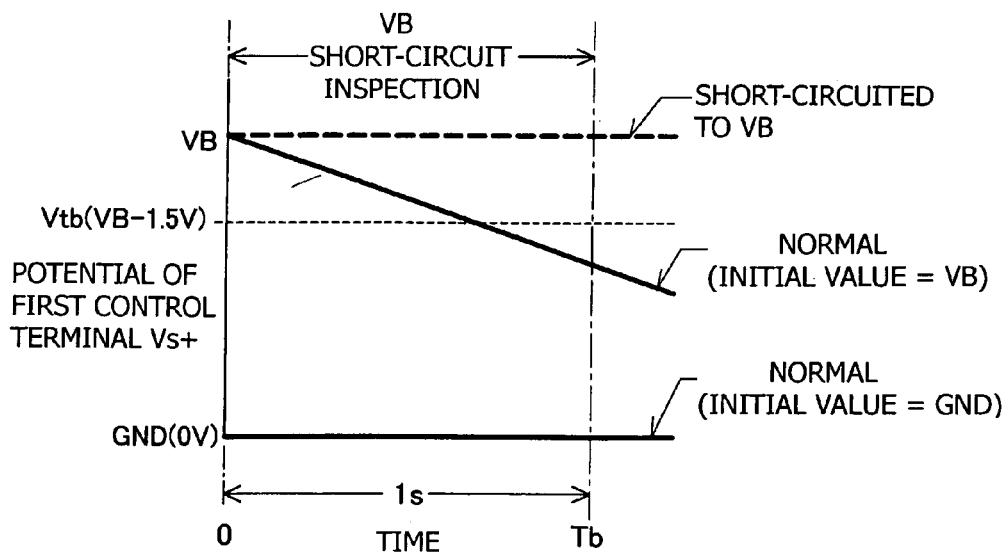
FIG. 4 is a graph showing a change in the potential of the first control terminal Vs+ of the gas-sensor control circuit obtained in Inspection Example 2 which was performed using the gas detection system of the first embodiment so as to inspect whether the first control terminal Vs+ is short-circuited to the power-source potential.

FIG. 4 is a graph showing the results of an inspection in which the negative-direction inspection current In was supplied to the first control terminal Vs+ by use of the constant current source 43N in order to determine whether or not the first control terminal Vs+ is short-circuited to the power source potential VB. The vertical direction represents potential, and the horizontal direction represents time. In FIG. 4, each solid line represents the potential of the first control terminal Vs+ in a normal state; and a broken line represents a change in the potential of the first control terminal Vs+ in the case where the first control terminal Vs+ is short-circuited to the power source potential VB.

In a normal state; i.e., when the first control terminal Vs+ (wiring line L1) is not short-circuited to the power source potential VB, if the initial value of the potential of the first control terminal Vs+ is the power source potential VB, the potential of the first control terminal Vs+ gradually decreases from the power source potential VB toward the ground potential GND. At this time, since the impedance of the gas-sensor control circuit 5 as viewed from the second control terminal COM and the third control terminal Ip+ is made high, even when the constant current source 43N is caused to supply the negative-direction inspection current In, this current In does not flow into the gas-sensor control circuit 5 from the second control terminal COM or the third control terminal Ip+. Accordingly, the negative-direction inspection current In is used to charge (discharge) the capacitor connected to the first control terminal Vs+, so that the potential of the first control terminal Vs+ decreases gradually.

If the initial value of the potential of the first control terminal Vs+ is the ground potential GND, the potential of the first control terminal Vs+ is maintained at the ground potential GND and does not change. This is because the constant current source 43N cannot generate a potential that is lower than the ground potential GND as described above.

In contrast, at the time of forming a short circuit; i.e., when the first control terminal Vs+ is short-circuited to the power source potential VB, the potential of the first control terminal Vs+ is maintained at the power source potential VB or a value close to the power source potential VB. This is because the negative-direction inspection current In flows through a conductive path formed by the short circuit.

Notably, in the first embodiment, when a short-circuit to the power source potential is inspected, the quantity of current that flows to the power source potential is limited by means of the constant current source 43N so as to prevent excess flow of current and resultant consumption of large electrical power during the short-circuit inspection.

According, inspection for determining whether or not the first control terminal Vs+ is short-circuited to the power source potential VB can be performed by determining whether the potential of the first control terminal Vs+ is lower than a power-source-short-circuit threshold potential Vtb (power source potential VB−1.5 V in the first embodiment), when a predetermined period of time Tb (1 second in the present example) has elapsed after start of supply of the negative-direction inspection current In to the first control terminal Vs+.

INSPECTION EXAMPLE 3

Figure 5:
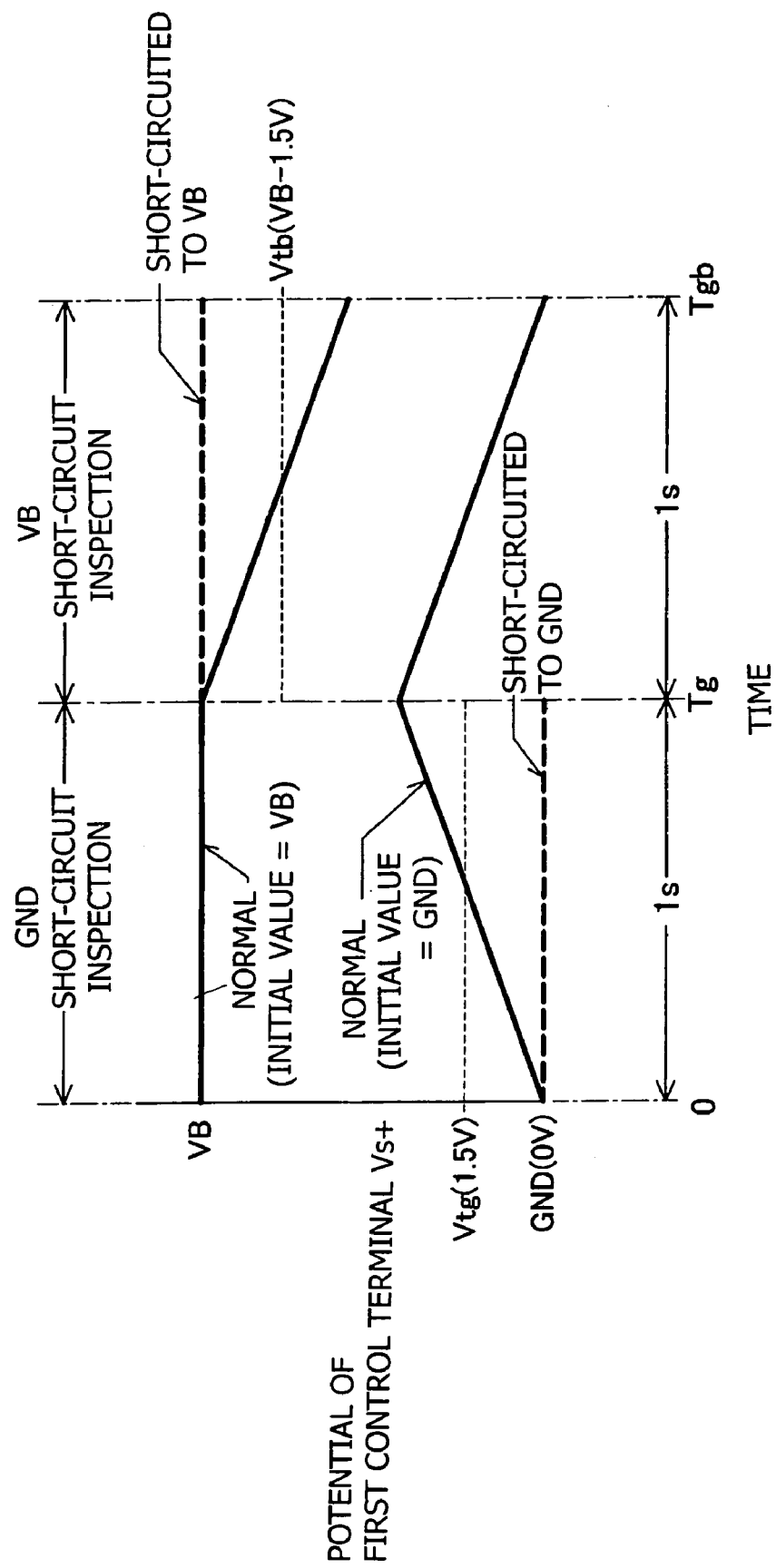
FIG. 5 is a graph showing a change in the potential of the first control terminal Vs+ of the gas-sensor control circuit obtained in Inspection Example 3 which was performed using the gas detection system of the first embodiment so as to inspect whether the first control terminal Vs+ is short-circuited to the ground potential and to then inspect whether the first control terminal Vs+ is short-circuited to the power-source potential.

Inspection for Short Circuit to the Ground Potential+Inspection for Short Circuit to the Power Source Potential FIG. 5 is a graph showing the results of an inspection in which the positive-direction inspection current Im was supplied to the first control terminal Vs+ by means of the constant current source 43M in order to determine whether or not the first control terminal Vs+ is short-circuited to the ground potential GND, and the negative-direction inspection current In was then supplied to the first control terminal Vs+ by use of the constant current source 43N in order to determine whether or not the first control terminal Vs+ is short-circuited to the power source potential VB.

In FIG. 5, each solid line represents a change in the potential in a normal state, and each broken line represents a change in the potential at the time of forming a short circuit. A first half (left half in FIG. 5) of the broken line represents a change in the potential of the first control terminal Vs+ in the case where the first control terminal Vs+ is short-circuited to the ground potential GND. A second half (right half in FIG. 5) of the broken line represents a change in the potential of the first control terminal Vs+ in the case where the first control terminal Vs+ is short-circuited to the power source potential VB.

The operation in the first half is similar to that shown in the graph of FIG. 3. That is, in a normal state, if the initial value of the potential of the first control terminal Vs+ is the ground potential GND, the potential of the first control terminal Vs+ gradually changes from the ground potential GND toward the power source potential VB. If the initial value of the potential of the first control terminal Vs+ is the power source potential VB, the potential of the first control terminal Vs+ is maintained at the power source potential VB and does not change. Notably, when the first control terminal Vs+ is short-circuited to the power source potential VB, the potential of the first control terminal Vs+ is maintained at the power source potential.

In contrast, when the first control terminal Vs+ is short-circuited to the ground potential GND, the potential of the first control terminal Vs+ is maintained at the ground potential GND and does not change. Accordingly, determination as to whether or not the first control terminal Vs+ is short-circuited to the ground potential can be performed at this stage.

After that (in the second half after elapse of a first predetermined period of time Tg), in a normal state, the potential of the first control terminal Vs+ gradually changes toward the ground potential GND irrespective of its initial value.

In contrast, when the first control terminal Vs+ is short-circuited to the power source potential VB, the potential of the first control terminal Vs+ is maintained at the power source potential VB.

Accordingly, in the first half, the inspection for determining whether or not the first control terminal Vs+ is short-circuited to the ground potential GND can be performed by determining whether the potential of the first control terminal Vs+ is higher than the ground-short-circuit threshold potential Vtg (1.5 V in the first embodiment), when the first predetermined period of time Tg (1 second in the present example) has elapsed after start of supply of the positive-direction inspection current Im from the constant current source 43M to the first control terminal Vs+.

Subsequently, in the second half, the inspection for determining whether or not the first control terminal Vs+ is short-circuited to the power source potential VB can be performed by determining whether or not the potential of the first control terminal Vs+ is lower than the power-source-short-circuit threshold potential Vtb (power source potential VB−1.5 V in the first embodiment), when a second predetermined period of time Tgb (1 second in the present example) has elapsed after start of supply of the negative-direction inspection current In from the constant current source 43N to the first control terminal Vs+ (after elapse of the first predetermined period of time Tg).

INSPECTION EXAMPLE 4

Figure 6:
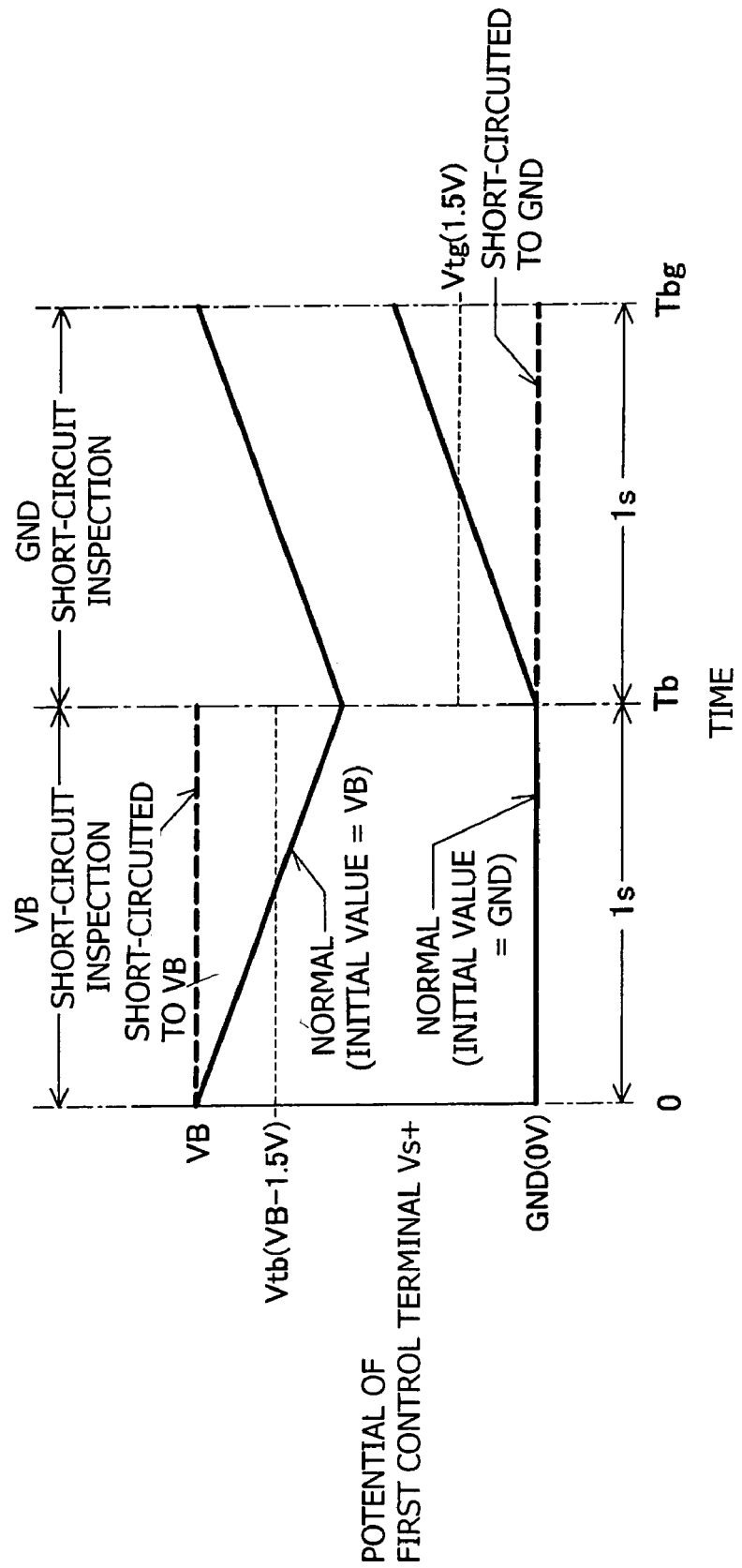
FIG. 6 is a graph showing a change in the potential of the first control terminal Vs+ of the gas-sensor control circuit obtained in Inspection Example 4 which was performed using the gas detection system of the first embodiment so as to inspect whether the first control terminal Vs+ is short-circuited to the power-source potential and to then inspect whether the first control terminal Vs+ is short-circuited to the ground potential.

Inspection for Short Circuit to the Power Source Potential+Inspection for Short Circuit to the Ground Potential FIG. 6 is a graph showing the results of an inspection in which the two inspections are performed in a sequence reverse to that in the case shown in FIG. 5. That is, FIG. 6 is a graph showing the results of an inspection in which the negative-direction inspection current In was supplied to the first control terminal Vs+ by use of the constant current source 43N in order to determine whether or not the first control terminal Vs+ is short-circuited to the power source potential VB, and the positive-direction inspection current Im was then supplied to the first control terminal Vs+ by use of the constant current source 43M in order to determine whether or not the first control terminal Vs+ is short-circuited to the ground potential GND.

In FIG. 6, each solid line represents a change in the potential in a normal state, and each broken line represents a change in the potential at the time of formation of a short circuit. A first half (left half in FIG. 6) of the broken line represents a change in the potential of the first control terminal Vs+ in the case where the first control terminal Vs+ is short-circuited to the power source potential VB. A second half (right half in FIG. 6) of the broken line represents a change in the potential of the first control terminal Vs+ in the case where the first control terminal Vs+ is short-circuited to the ground potential GND.

The operation in the first half is similar to that shown in the graph of FIG. 4. That is, in a normal state, if the initial value of the potential of the first control terminal Vs+ is the ground potential GND, the potential of the first control terminal Vs+ is maintained at the ground potential GND and does not change. If the initial value of the potential of the first control terminal Vs+ is the power source potential VB, the potential of the first control terminal Vs+ gradually changes from the power source potential VB to the ground potential GND. Notably, when the first control terminal Vs+ is short-circuited to the ground potential, the potential of the first control terminal Vs+ is maintained at the ground potential.

In contrast, when the first control terminal Vs+ is short-circuited to the power source potential VB, the potential of the first control terminal Vs+ is maintained at the power source potential VB and does not change. Accordingly, determination as to whether or not the first control terminal Vs+ is short-circuited to the power source potential can be performed at this stage.

After that (in the second half after elapse of the first predetermined period of time Tb), in a normal state, the potential of the first control terminal Vs+ gradually changes toward the power source potential VB irrespective of its initial value.

In contrast, when the first control terminal Vs+ is short-circuited to the ground potential, the potential of the first control terminal Vs+ is maintained at the ground potential GND.

Accordingly, in the first half, the inspection for determining whether or not the first control terminal Vs+ is short-circuited to the power source potential VB can be performed by determining whether the potential of the first control terminal Vs+ is lower than the power-source-short-circuit threshold potential Vtb (power source potential VB−1.5 V in the first embodiment), when the first predetermined period of time Tb (1 second in the present example) has elapsed after start of supply of the negative-direction inspection current In from the constant current source 43N to the first control terminal Vs+.

Subsequently, in the second half, the inspection for determining whether or not the first control terminal Vs+ is short-circuited to the ground potential GND can be performed by determining whether the potential of the first control terminal Vs+ is higher than the ground-short-circuit threshold potential Vtg (1.5 V in the first embodiment), when the second predetermined period of time Tbg (1 second in the present example) has elapsed after start of supply of the positive-direction inspection current Im from the constant current source 43M to the first control terminal Vs+ (after elapse of the first predetermined period of time Tb).

In some cases, an unillustrated capacitor is connected to the first control terminal Vs+ for noise suppression. In such case, the change in the potential of the first control terminal Vs+ with time becomes slower due to charging and discharging of the capacitor. Therefore, the predetermined period of time (first predetermined period of time) Tg, Tb or the second predetermined period of time Tgb, Tbg for waiting before determining whether or not a short circuit is formed is preferably set to be longer than in the above-described case. Alternatively, the ground-short-circuit threshold potential Vtg is preferably set to a lower value, and the power-source-short-circuit threshold potential Vtb is preferably set to a higher value. In this manner, the predetermined periods of time Tg, etc., for waiting and the threshold potentials Vtg, etc. are properly set such that a normal state and a short-circuited state can be distinguished from each other accurately.

Figure 7:
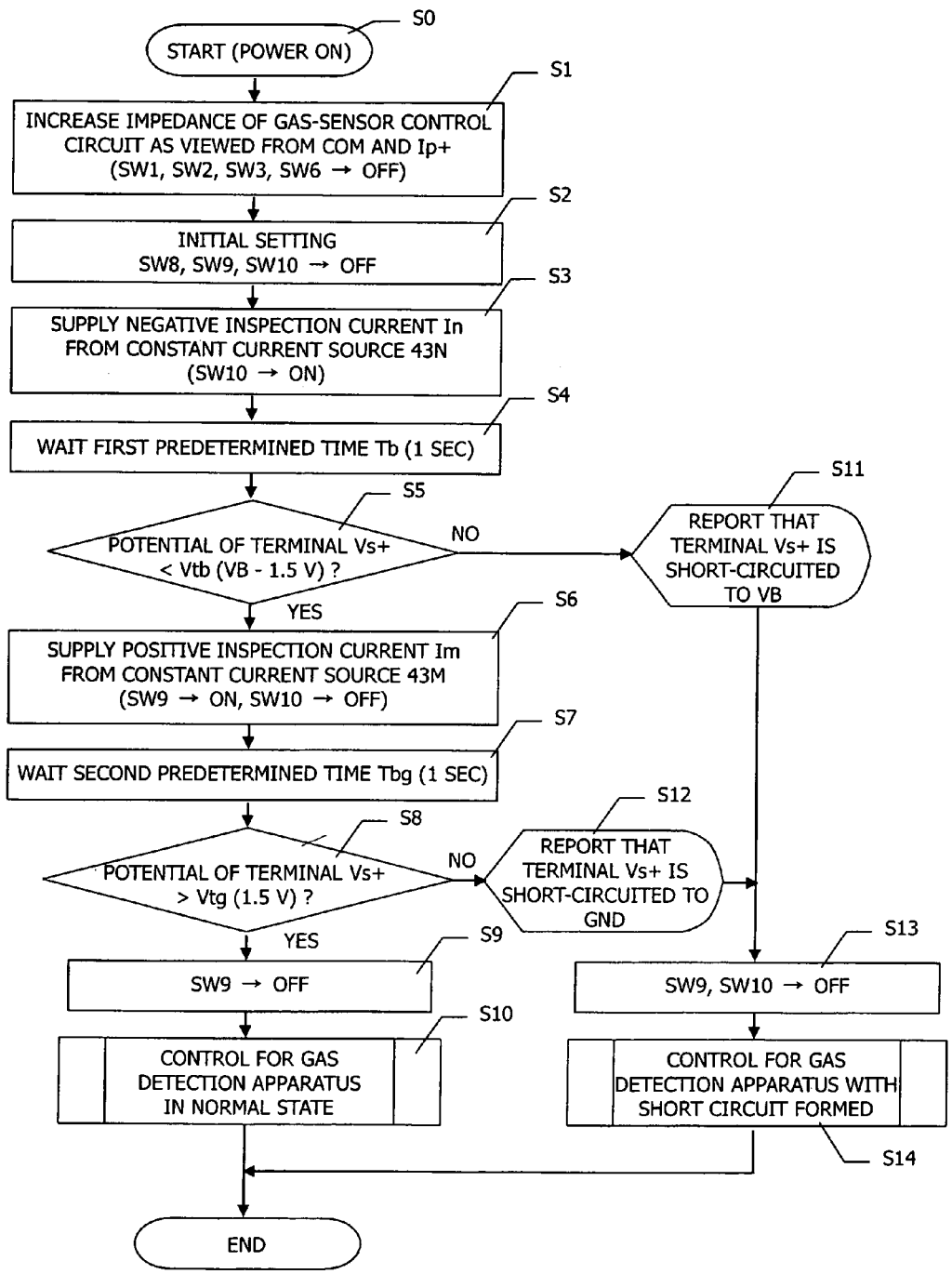
FIG. 7 is a flowchart showing the steps of an inspection method employed in Inspection Example 3 which was performed using the gas detection system of the first embodiment so as to inspect whether the first control terminal Vs+ of the gas-sensor control circuit is short-circuited to the ground potential and to then inspect whether the first control terminal Vs+ is short-circuited to the power-source potential.

Next, with reference to FIGS. 6 and 7, the specific steps of an inspection method performed in the gas detection system 1 of the first embodiment for Inspection Example 4 will be described, in which presence or absence of a short circuit of the first control terminal Vs+ to the power source potential VB is checked, and presence or absence of a short circuit of the first control terminal Vs+ to the ground potential GND is then checked.

First, immediately after the power of the gas detection system 1 is turned on in step S0, the microcomputer 3 proceeds to step S1.

In step S1, the microcomputer 3 makes the impedance of the gas-sensor control circuit 5 high as viewed from the second control terminal COM and the third control terminal Ip+ for which short-circuit inspection is not performed (uninspected terminals) among the control terminals of the gas-sensor control circuit 5 (uninspected-terminal-impedance increasing step).

Specifically, the microcomputer 3 turns the switches SW1 and SW2 off so as to cut off the output terminals of the operational amplifiers 34 and 36 from the second control terminal COM. In addition, the microcomputer 3 turns the switches SW3 and SW6 off so as to cut off the electrical connections between the third control terminal Ip+ and the operational amplifier 32 and the ground potential GND. When the respective switches are turned off in this manner, the impedance of the gas-sensor control circuit 5 as viewed from the second control terminal COM and the third control terminal Ip+ becomes high.

In step S2, the microcomputer 3 turns the switches SW8, SW9, and SW10 off as an initial setting.

In step S3, the microcomputer 3 turns on the switch SW10 connected to the output terminal of the constant current source 43N so that the negative-direction inspection current In flows from the first element terminal 4T1 toward the first control terminal Vs+ of the gas-sensor control circuit 5 (inspection current supply step, first inspection current supply step). As a result, the potential of the first control terminal Vs+ of the gas-sensor control circuit 5 changes as shown in the first half of FIG. 6, depending on whether or not a short-circuit is formed.

In step S4, the microcomputer 3 waits the first predetermined period of time Tb (1 second in the present example) by use of an unillustrated timer of the microcomputer 3 (waiting step, first waiting step).

In step S5, the microcomputer 3 determines whether the potential of the first control terminal Vs+ measured by means of the potential monitor circuit 41 is lower than the power-source-short-circuit threshold potential Vtb (power source potential VB−1.5 V in the present example) (short-circuit determination step, first determination step). Specifically, this determination is performed by comparing the power-source-short-circuit threshold potential Vtb and a digital value obtained through conversion of the potential of the first control terminal Vs+ by means of the potential monitor circuit 41.

When the results of the comparison show that the potential of the first control terminal Vs+ is lower than the power-source-short-circuit threshold potential Vtb (Yes), the microcomputer 3 proceeds to step S6. Meanwhile, when the potential of the first control terminal Vs+ is not lower than the power-source-short-circuit threshold potential Vtb (No), the microcomputer 3 determines that the first control terminal Vs+ is short-circuited to the power source potential VB, and proceeds to step S11.

In the inspection method of the present example, the above-described step S4, serving as a waiting step, and step S5, serving as a short-circuit determination step, constitute a diagnosis step. Alternatively, the above-described step S4, serving as a first waiting step, and step S5, serving as a first determination step, constitute a first diagnosis step.

Subsequently, in step S6, the microcomputer 3 turns the switch SW10 off and turns the switch SW9 on, so as to enable the constant current source 43M to supply the positive-direction inspection current Im which flows from the first control terminal Vs+ toward the first element terminal 4T1 (second inspection current supply step). As a result, the potential of the first control terminal Vs+ of the gas-sensor control circuit 5 changes as shown in the second half of FIG. 6, depending on whether or not a short circuit is formed.

In step S7, the microcomputer 3 waits the second predetermined period of time Tbg (1 second in the present example) by use of an unillustrated timer of the microcomputer 3 (waiting step, second waiting step).

In step S8, the microcomputer 3 determines whether the potential of the first control terminal Vs+ measured by means of the potential monitor circuit 41 is higher than the ground-short-circuit threshold potential Vtg (1.5 V in the present example) (second determination step). Specifically, this determination is performed by comparing the ground-short-circuit threshold potential Vtg and a digital value obtained through conversion of the potential of the first control terminal Vs+ by means of the potential monitor circuit 41.

When the results of the comparison show that the potential of the first control terminal Vs+ is higher than the ground-short-circuit threshold potential Vtg (Yes), the microcomputer 3 determines that the first control terminal Vs+ is not short-circuited to the ground potential GND, and proceeds to step S9. Meanwhile, when the potential of the first control terminal Vs+ is not higher than the ground-short-circuit threshold potential Vtg (No), the microcomputer 3 determines that the first control terminal Vs+ is short-circuited to the ground potential GND, and proceeds to step S12.

In the inspection method of the present example, the above-described step S7, serving as a second waiting step, and step S8, serving as a second determination step, constitute a second diagnosis step.

In step S9, the microcomputer 3 turns the switch SW9 off so as to electrically cut off the output of the constant current source 43M.

Subsequently, in step S10, the microcomputer 3 performs control of the gas detection system 1 (the gas detection apparatus 2 and the gas sensor element 4) for a normal state, because the microcomputer 3 has determined that the first control terminal Vs+, or the wiring line L1 or the first element terminal 4T1 connected thereto, is not short-circuited to either the power source potential or the ground potential, and therefore, the gas detection system 1 is normal.

Meanwhile, when a "No" determination is made in step S5, in step S11, the microcomputer 3 reports that the first control terminal Vs+ is short-circuited to the power source potential VB, and then proceeds to step S13. When a "No" determination is made in step S8, in step S12, the microcomputer 3 reports that the first control terminal Vs+ is short-circuited to the ground potential GND, and then proceeds to step S13. In step S13, the microcomputer 3 turns the switches SW9 and SW10 off so as to cut off the output terminals of the constant current sources 43M and 43N from the first control terminal Vs+. Since the switch SW8 has already been turned off (step S2), the impedance of the gas-sensor control circuit 5 as viewed from the first control terminal Vs+ is also made high (inspected terminal impedance increasing step).

Further, in step S14, the microcomputer 3 performs control for the case where a short circuit is formed in the gas detection apparatus 2; e.g., turning the power of the gas-sensor control circuit 5 off, and providing to a driver or the like a warning that indicates occurrence of a short circuit, by means of sound, or turning on or flickering a lamp.

In the above, an inspection method has been described corresponding to Inspection Example 4 (see FIG. 6) in which presence or absence of a short circuit of the first control terminal Vs+ to the power source potential VB is checked, and presence or absence of a short circuit of the first control terminal Vs+ to the ground potential GND is then checked. However, inspection methods corresponding to other inspection examples shown in FIGS. 3, 4, and 5 can be performed in a similar manner.

For example, in the case of Inspection Example 3 (see FIG. 5) in which presence or absence of a short circuit of the first control terminal Vs+ to the ground potential GND is checked, and presence or absence of a short circuit of the first control terminal Vs+ to the power source potential VB is then checked, the above-described inspection method can be performed such that the steps S6 to S8 and S12 are first executed, and the steps S3 to S5 and S11 are then executed.

According to the short-circuit inspection method using the gas detection system 1 of the first embodiment, the impedance of the gas-sensor control circuit 5 as viewed from the second control terminal COM and the third control terminal Ip+ is rendered high, so that even when the inspection current Im or In is supplied to the first control terminal Vs+, the inspection current does not flow through the gas sensor element 4. Accordingly, the inspection for the first control terminal Vs+ can be properly performed, without causing a problem such as blackening of the gas sensor element 4, which would otherwise occur because of current flowing through the gas sensor element 4 during the short-circuit inspection.

When the first control terminal Vs+ is determined to be short-circuited to the ground potential GND or the power source potential VB, in step S13, the microcomputer 3 turns the switches SW9 and SW10 off so as to make the impedance of the gas-sensor control circuit 5 high as viewed from the first control terminal Vs+. That is, the gas sensor element 4 is electrically cut off from the gas-sensor control circuit 5. Therefore, after that, a malfunction of the gas sensor element 4 caused by current flowing excessively or in an improper (reverse) direction can be prevented with certainty, up to a point when a measure against the short circuit is taken and the short-circuited state is eliminated.

Further, the short-circuit inspection for the first control terminal Vs+ is performed immediately after the power of the gas detection system 1 is turned on in step S0; and when the first control terminal Vs+ is short-circuited to the ground potential GND or the power source potential VB, the gas sensor element 4 is electrically cut off from the gas-sensor control circuit 5 in step S13. Therefore, when a short circuit is present, the short-circuit inspection can be ended without current flowing through the gas sensor element 4. Therefore, it is possible to prevent with certainty occurrence of a malfunction of the gas sensor element 4, which would otherwise be caused by current which flows excessively or in an improper (reverse) direction because of the short circuit.

Second Embodiment

Next, a gas detection system 1A according to a second embodiment of the present invention will be described with reference to FIG. 1 and FIGS. 8 to 10.

The gas detection system 1A according to the second embodiment is identical to the gas detection system 1 of the first embodiment except that in place of the gas-sensor control circuit 5 (see FIG. 2) of the gas detection system 1, a gas-sensor control circuit 5A is used. That is, like the gas detection system 1 of the first embodiment, the gas detection system 1A includes a microcomputer 3, a gas sensor element 4, a heater control circuit 6, and a heater 7.

In the following description, the portions which differ from those of the first embodiment will be mainly described, and descriptions of the remaining portions will be simplified or omitted.

Figure 8:
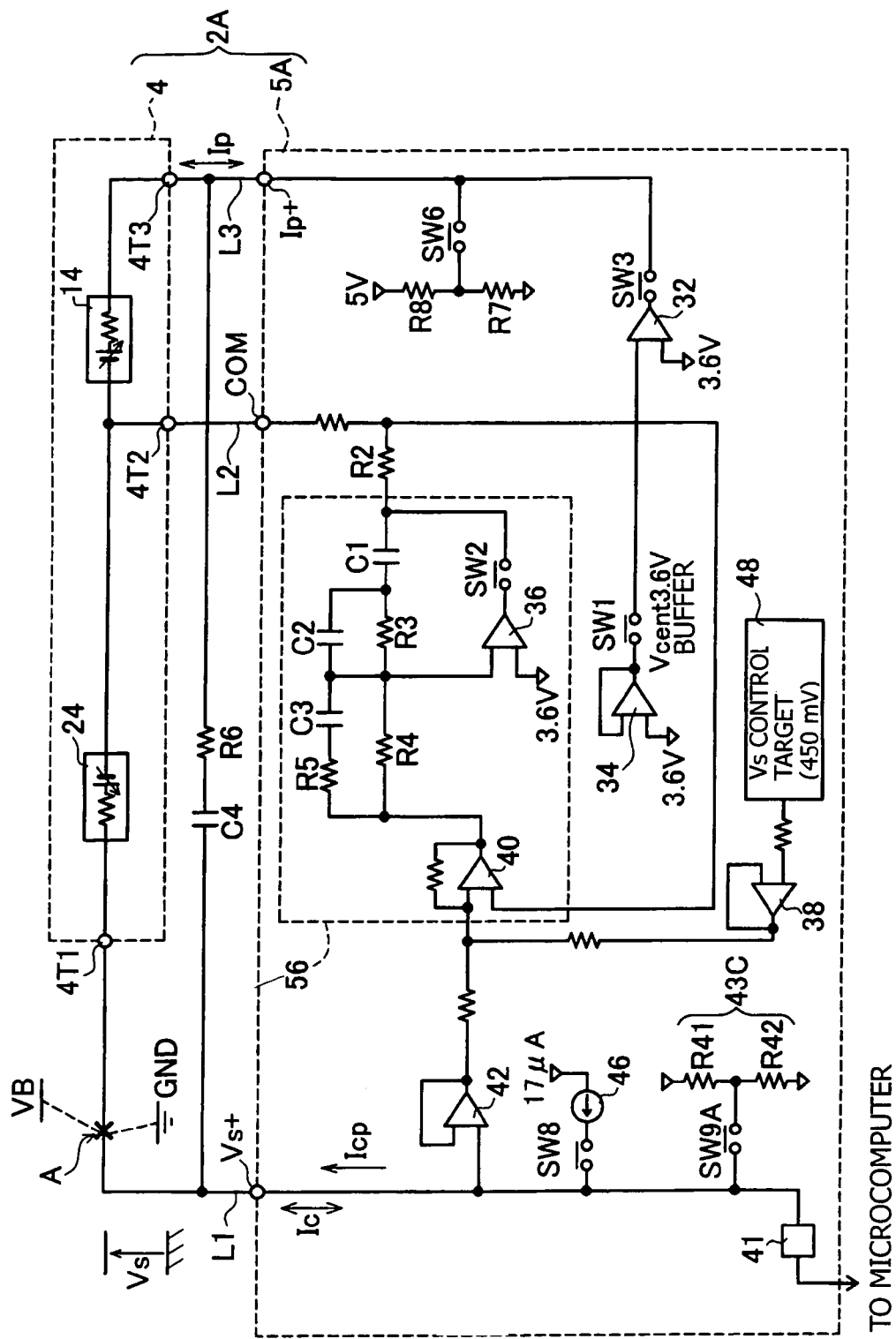
FIG. 8 is a circuit diagram showing the circuit configuration of a gas detection apparatus according to the second embodiment.

First, the gas-sensor control circuit 5A will be described with reference to FIG. 8.

The gas-sensor control circuit 5 of the first embodiment includes the constant current sources 43M and 43N as an inspection current supply circuit. In contrast, in the gas-sensor control circuit 5A of the second embodiment, an inspection current is supplied to the first control terminal Vs+ by means of a pull-up-down circuit 43C which includes resistor elements R41 and R42 and divides the potential difference between the power source potential and the ground potential. A switch SW9A is interposed between the pull-up-down circuit 43C and the first control terminal Vs+. The pull-up-down circuit 43C can be electrically cut off from the first control terminal Vs+ by turning the switch SW9A off. The gas-sensor control circuit 5A is identical with the gas-sensor control circuit 5 of the first embodiment except that the inspection current supply circuit is formed by the pull-up-down circuit 43C and the switch SW9A.

The pull-up-down circuit 43C supplies an inspection current Ic to the first control terminal Vs+ so as to determine whether the first control terminal Vs+ is short-circuited to the ground potential GND or the power source potential VB. The pull-up-down circuit 43C supplies an inspection current Ic to the first control terminal Vs+ such that when the first control terminal Vs+ is not short-circuited to either the ground potential GND or the power source potential VB, the potential of the first control terminal Vs+ becomes equal to an intermediate potential VC between the ground potential GND and the power source potential VB, which is determined by the resistor elements R41 and R42.

INSPECTION EXAMPLE 5

Inspection for Short Circuit to the Power Source Potential and the Ground Potential Next, a change in the potential of the first control terminal Vs+ when the inspection current Ic is supplied to the first control terminal Vs+ and a method for inspecting the first control terminal Vs+ will be described with reference to FIGS. 9 and 10.

First, immediately after the power of the gas detection system 1A is turned on in step S100, the microcomputer 3 proceeds to step S1. In step S1, which is identical with step S1 of the inspection method performed by the gas detection system 1 of the first embodiment, the microcomputer 3 makes the impedance of the gas-sensor control circuit 5A high as viewed from the second control terminal COM and the third control terminal Ip+ (uninspected-terminal-impedance increasing step).

Subsequently, in step S102, the microcomputer 3 turns the switches SW8 and SW9A off as an initial setting.

In step S103, the microcomputer 3 turns the switch SW9A on so that the inspection current Ic flows from the pull-up-down circuit 43C (inspection current supply step). The flow direction of the inspection current Ic changes depending on the potential of the first control terminal Vs+.

Figure 9:
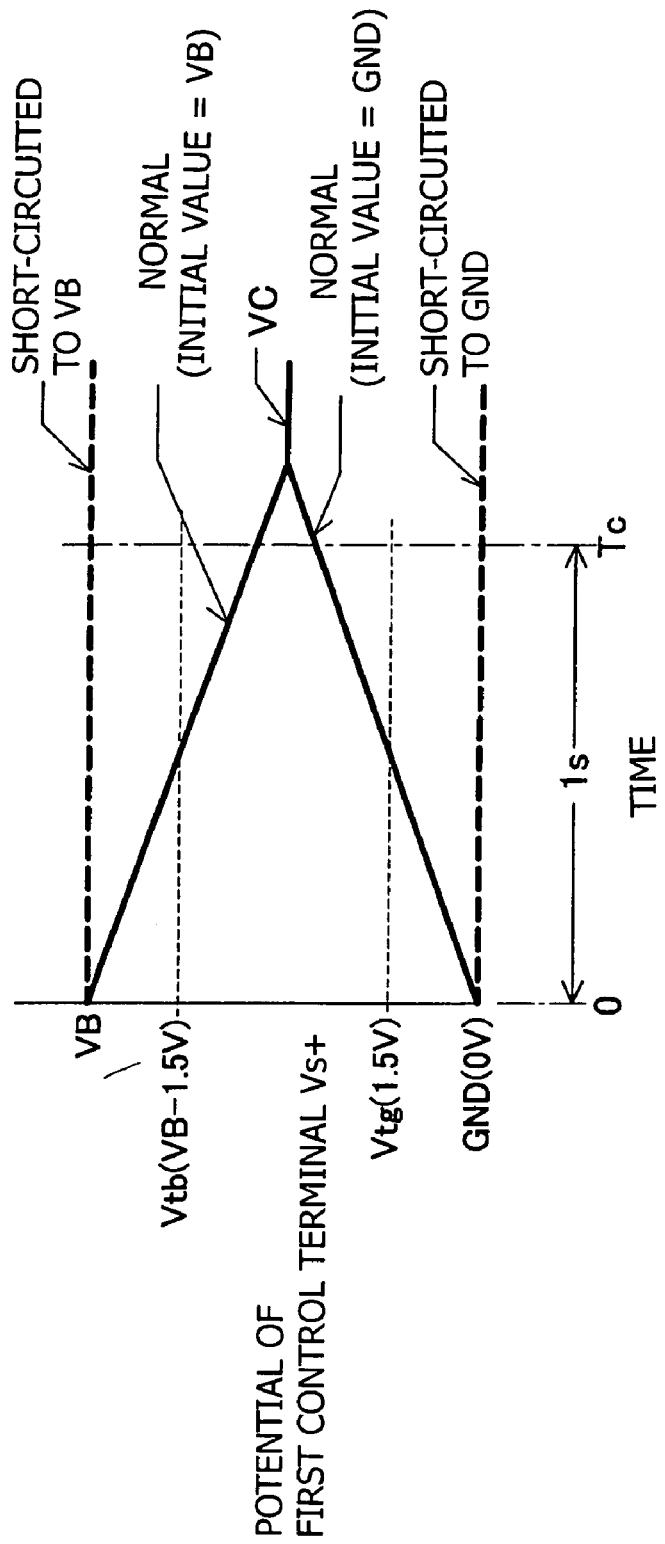
FIG. 9 is a graph showing a change in the potential of the first control terminal Vs+ of the gas-sensor control circuit obtained in Inspection Example 5 which was performed using the gas detection system of the second embodiment so as to inspect whether the first control terminal Vs+ is short-circuited to the ground potential or to the power-source potential.
Figure 10:
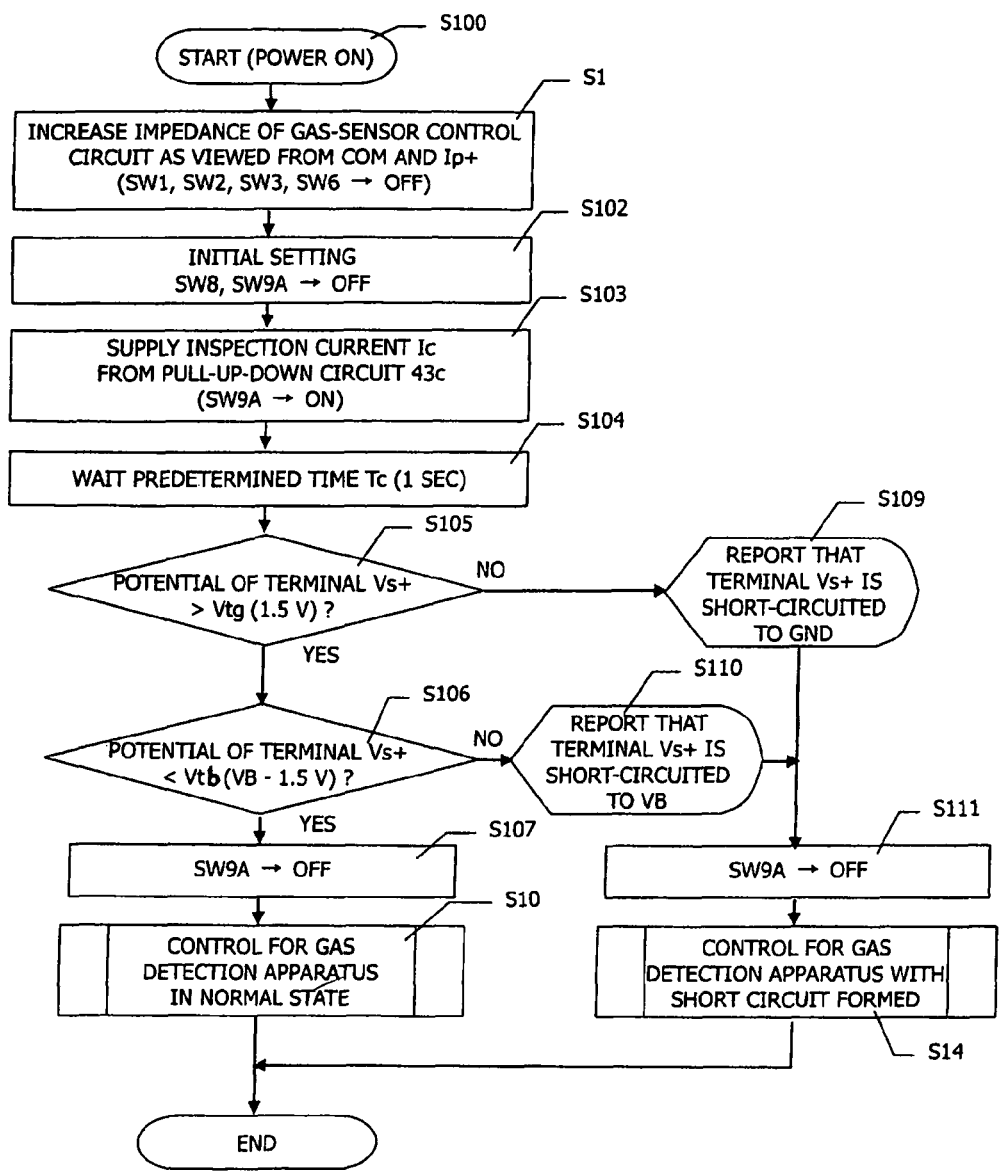
FIG. 10 is a flowchart showing the steps of an inspection method employed in Inspection Example 5 which was performed using the gas detection system of the second embodiment so as to inspect whether the first control terminal Vs+ of the gas-sensor control circuit is short-circuited to the ground potential or to the power-source potential.

FIG. 9 is a graph showing changes in the potential of the first control terminal Vs+ at the time when the inspection current Ic is supplied to the first control terminal Vs+. In the graph of FIG. 9, each solid line represents a change in the potential of the first control terminal Vs+ in a normal state in which no short circuit is formed; and each broken line represents a change in the potential of the first control terminal Vs+ in the case where the first control terminal Vs+ is short-circuited. Notably, at the time of start of inspection, the potential of the first control terminal Vs+ can assume any initial value between the power source potential VB and the ground potential GND. Therefore, the graph shows the case where the initial value is the power source potential and the case where the initial value is the ground potential.

In a normal state, if the initial value of the potential of the first control terminal Vs+ is the ground potential GND, the potential of the first control terminal Vs+ gradually changes from the ground potential GND toward the intermediate potential VC. If the initial value of the potential of the first control terminal Vs+ is the power source potential VB, the potential of the first control terminal Vs+ gradually changes from the power source potential VB toward the intermediate potential VC.

Meanwhile, if the first control terminal Vs+ is short-circuited to the ground potential GND, the potential of the first control terminal Vs+ is maintained at the ground potential GND. If the first control terminal Vs+ is short-circuited to the power source potential VB, the potential of the first control terminal Vs+ is maintained at the power source potential VB.

In step S104, the microcomputer 3 waits a predetermined period of time Tc (1 second in the present example) by use of an unillustrated timer of the microcomputer 3 (waiting step).

Subsequently, in step S105, the microcomputer 3 determines whether the potential of the first control terminal Vs+ measured by means of the potential monitor circuit 41 is higher than the ground-short-circuit threshold potential Vtg (1.5 V in the present example). Specifically, this determination is performed by comparing the ground-short-circuit threshold potential Vtg and a digital value obtained through conversion of the potential of the first control terminal Vs+ by means of the potential monitor circuit 41.

When the results of the comparison show that the potential of the first control terminal Vs+ is higher than the ground-short-circuit threshold potential Vtg (Yes), the microcomputer 3 determines that a short circuit to the ground potential GND is not formed, and proceeds to step S106. Meanwhile, when the potential of the first control terminal Vs+ is not higher than the ground-short-circuit threshold potential Vtg (No), the microcomputer 3 determines that the first control terminal Vs+ is short-circuited to the ground potential GND, and proceeds to step S109.

Moreover, in step S106, the microcomputer 3 determines whether the potential of the first control terminal Vs+ measured by means of the potential monitor circuit 41 is lower than the power-source-short-circuit threshold potential Vtb (VB−1.5 V in the present example). Specifically, this determination is performed by comparing the power-source-short-circuit threshold potential Vtb and the digital value of the potential of the first control terminal Vs+.

When the results of the comparison show that the potential of the first control terminal Vs+ is lower than the power-source-short-circuit threshold potential Vtb (Yes), the microcomputer 3 determines that a short circuit to the power source potential VB is not formed; i.e., the gas detection system 1A is normal, and proceeds to step S107. Meanwhile, when the potential of the first control terminal Vs+ is not lower than the power-source-short-circuit threshold potential Vtb (No), the microcomputer 3 determines that the first control terminal Vs+ is short-circuited to the power source potential VB, and proceeds to step S110.

In step S107, the microcomputer 3 turns the switch SW9A off so as to electrically cut off the output of the pull-up-down circuit 43C from the first control terminal Vs+.

After that, as in the first embodiment, in step S10, the microcomputer 3 performs control of the gas detection system 1A (the gas detection apparatus 2A and the gas sensor element 4) for a normal state, because the microcomputer 3 has determined that the first control terminal Vs+, or the wiring line L1 or the first element terminal 4T1 connected thereto is not short-circuited to either the power source potential or the ground potential, and therefore, the gas detection system 1A is normal.

Meanwhile, when a "No" determination is made in step S105, in step S109, the microcomputer 3 reports that the first control terminal Vs+ is short-circuited to the ground potential GND, and then proceeds to step S111. When a "No" determination is made in step S106, in step S110, the microcomputer 3 reports that the first control terminal Vs+ is short-circuited to the power source potential VB, and then proceeds to step S111.

In step S111, the microcomputer 3 turns the switches SW9A off so as to cut off the output of the pull-up-down circuit 43C from the first control terminal Vs+. Since the switch SW8 has already been turned off in step S102, the impedance of the gas-sensor control circuit 5A as viewed from the first control terminal Vs+ is also made high (inspected terminal impedance increasing step).

After that, in step S14, as in the case of the first embodiment, the microcomputer 3 performs control for the case where a short circuit is formed in the gas detection apparatus 2A; e.g., turning the power of the gas-sensor control circuit 5A off, and providing to a driver or the like a warning that indicates the occurrence of a short circuit by means of sound, or turning on or flickering a lamp.

According to the short-circuit inspection method using the gas detection system 1A of the second embodiment, formation of a short circuit to the ground potential GND or the power source potential VB can be determined merely by supplying a single type of inspection current Ic. Therefore, inspection can be performed simply and quickly in order to determine whether or not a short circuit is present.

In the above-described Inspection Example 5, a short circuit to the ground potential GND is first determined (step S105), and a short circuit to the power source potential VB is then determined (step S106). However, these determinations can be performed in the reverse order.

Third Embodiment

Figure 11:
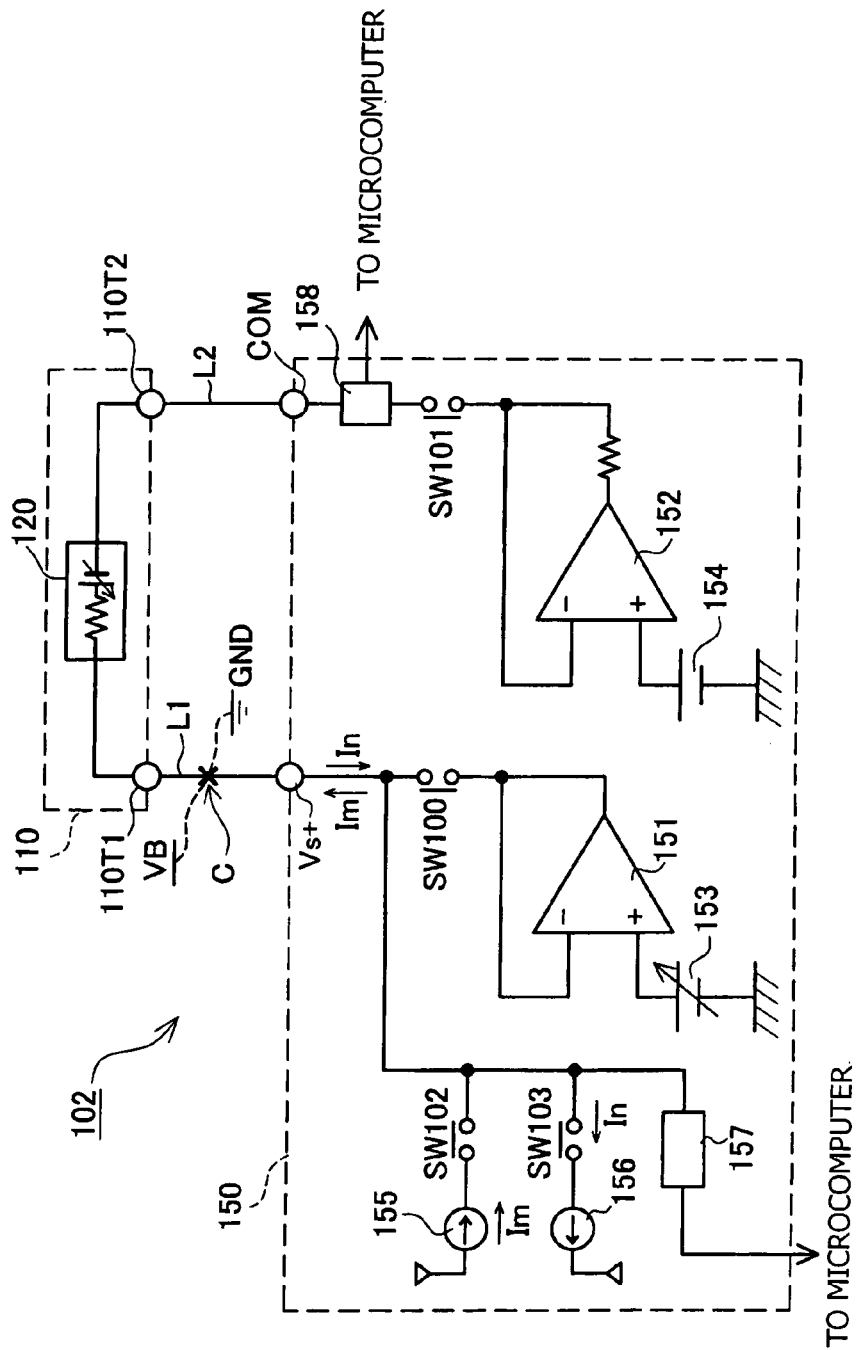
FIG. 11 is a circuit diagram showing the circuit configuration of a gas detection apparatus according to a third embodiment.

Next, a gas detection system according to a third embodiment of the present invention will be described with reference to FIGS. 11 to 13.

The gas detection system for measuring a measured gas within exhaust gas includes a gas detection apparatus 102 composed of a gas sensor element 110 and a gas-sensor control circuit 150. Although not illustrated, this gas detection system includes a heater for maintaining the gas sensor element 110 at an operation temperature, a heater control circuit for controlling the heater, and a microcomputer. Since the heater, the heater control circuit, and the microcomputer are the same as those of the first and second embodiments, their descriptions are omitted.

The gas sensor element 110, which is disposed in the exhaust gas system of a gasoline engine, includes a detection cell 120, which is formed into a thin plate-like shape from zirconia, which is oxygen-ion conductive solid electrolyte, and a pair of platinum electrodes formed on the opposite surfaces of the detection cell 120. The electrodes sandwiching the detection cell 120 are connected to first and second element terminals 110T1 and 110T2 of the gas sensor element 110, respectively.

The gas-sensor control circuit 150 has a first control terminal Vs+ and a second control terminal COM, which are connected to the element terminals 110T1 and 110T2 via the wiring lines L1 and L2. This gas-sensor control circuit 150 controls the gas sensor element 110, and detects the oxygen concentration of the measured gas.

In the gas-sensor control circuit 150, a circuit connected to the first control terminal Vs+ will first be described. The output terminals of an operational amplifier 151 and constant current sources 155 and 156 are connected to the first control terminal Vs+ via the switches SW100, SW102, and SW103, respectively. Further, a potential monitor circuit 157 for measuring the potential of the first control terminal Vs+ is connected to the first control terminal Vs+.

A variable voltage source 153 whose output potential is adjustable is connected to the non-inverted input terminal of the operational amplifier 151, so that the operational amplifier 151 outputs toward the first control terminal Vs+ a potential generated by the variable voltage source 153. When the switch SW100 is turned off, the impedance of the operational amplifier 151 as viewed from the first control terminal Vs+ can be made high.

The constant current source 155 supplies a positive-direction inspection current Im which flows out of the first control terminal Vs+. Meanwhile, the constant current source 156 supplies a negative-direction inspection current In which flows in a direction opposite the flow direction of the positive-direction inspection current Im. The impedances of the constant current sources 155 and 156 as viewed from the first control terminal Vs+ can be made high (a state equivalent to a state where the constant current sources 155 and 156 are cut off) by turning the switches SW102 and SW103 off.

Meanwhile, the input terminal of the potential monitor circuit 157 is connected directly to the first control terminal Vs+. The input terminal of the potential monitor circuit 157 always assumes a high impedance as viewed from the first control terminal Vs+. As in the case of the potential monitor circuit 41 of the first embodiment, the potential monitor circuit 157 includes a known A/D converter, and converts the potential of the first control terminal Vs+ to a digital value, which is then fed to the microcomputer.

Therefore, when all the switches SW100, SW102, and SW103 are turned off, the impedance of the gas-sensor control circuit 150 is high as viewed from the first control terminal Vs+. That is, in this case, the gas-sensor control circuit 150 can be seen to be electrically cut off from the first control terminal Vs+.

Next, in the gas-sensor control circuit 150, a circuit connected to the second control terminal COM will be described. An operational amplifier 152 is connected to the second control terminal COM via a gas concentration output circuit 158.

The gas concentration output circuit 158 includes a known A/D converter, and outputs to the microcomputer a digital value corresponding to a current flowing through a current detection resistor.

A constant voltage source 154 for generating a constant potential is connected the non-inverted input terminal of the operational amplifier 152, so that the operational amplifier 152 outputs the potential generated by the constant voltage source 154.

The output terminal of the operational amplifier 152 is connected to the gas concentration output circuit 158 via a switch SW101. As described above, the gas concentration output circuit 158 is formed by a current detection resistor. Therefore, through switching of the switch SW101, the impedances of the gas concentration output circuit 158 and the operational amplifier 152 as viewed from the second control terminal COM can be switched to low impedance or high impedance.

Therefore, when the switch SW101 is turned off, the gas-sensor control circuit 150 assumes a high impedance as viewed from the second control terminal COM. That is, in this case, the gas-sensor control circuit 150 can be electrically cut off from the second control terminal COM.

Next, a gas-concentration detection method using the gas detection system will be described.

The detection cell 120 is configured such that the current flowing through the detection cell 120 changes in accordance with the difference between the oxygen concentration of the measured gas in contact with one surface of the detection cell 120 and the oxygen concentration of a reference gas (e.g., outside air) in contact with the other surface of the detection cell 120. The detection cell 120 has characteristics such that when the concentration difference is constant, the current flowing through the detection cell 120 becomes generally constant irrespective of change in the voltage applied to the electrodes on the opposite surfaces of the detection cell 120. The gas detection system of the third embodiment detects gas concentration by use of a known method which utilizes such current characteristic of the detection cell 120. Specifically, in the gas-sensor control circuit 150, the output potential of the constant voltage source 154 is adjusted such that the voltage applied to the electrodes falls within a predetermined range, and the current flowing through the detection cell 120 is measured by use of the gas concentration output circuit 158, whereby the gas concentration is detected.

Like the gas detection apparatus 2 of the first embodiment, when a portion C electrically connected to the first control terminal Vs+ is short-circuited to the power source potential VB or the ground potential GND, current can flow through the detection cell 120 excessively or in an improper (reverse) direction to result in blackening or a rupture.

INSPECTION EXAMPLE 6

Figure 12:
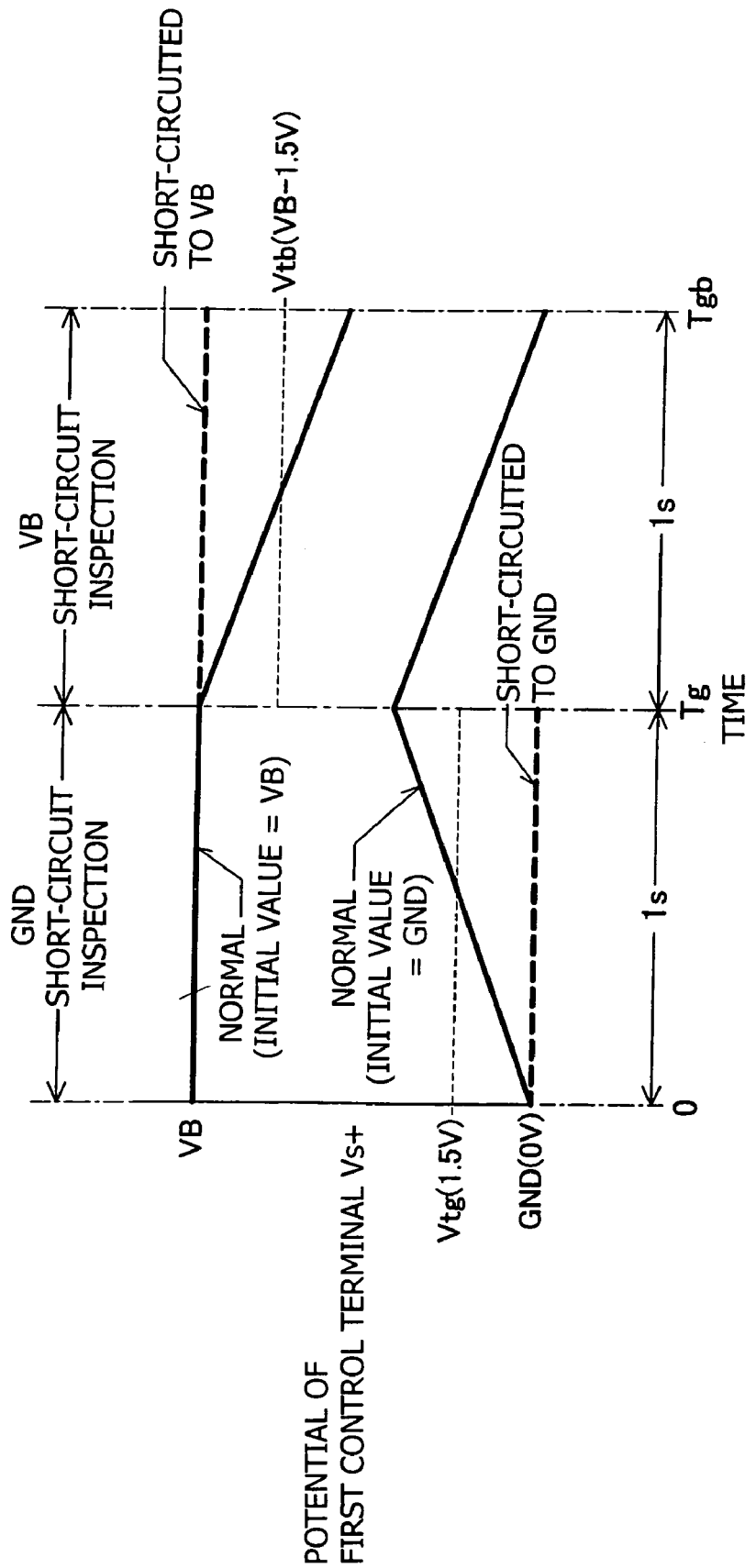
FIG. 12 is a graph showing a change in the potential of the first control terminal Vs+ of the gas-sensor control circuit obtained in Inspection Example 6 which was performed using the gas detection system of the third embodiment so as to inspect whether the first control terminal Vs+ is short-circuited to the ground potential and to then inspect whether the first control terminal Vs+ is short-circuited to the power-source potential.
Figure 13:
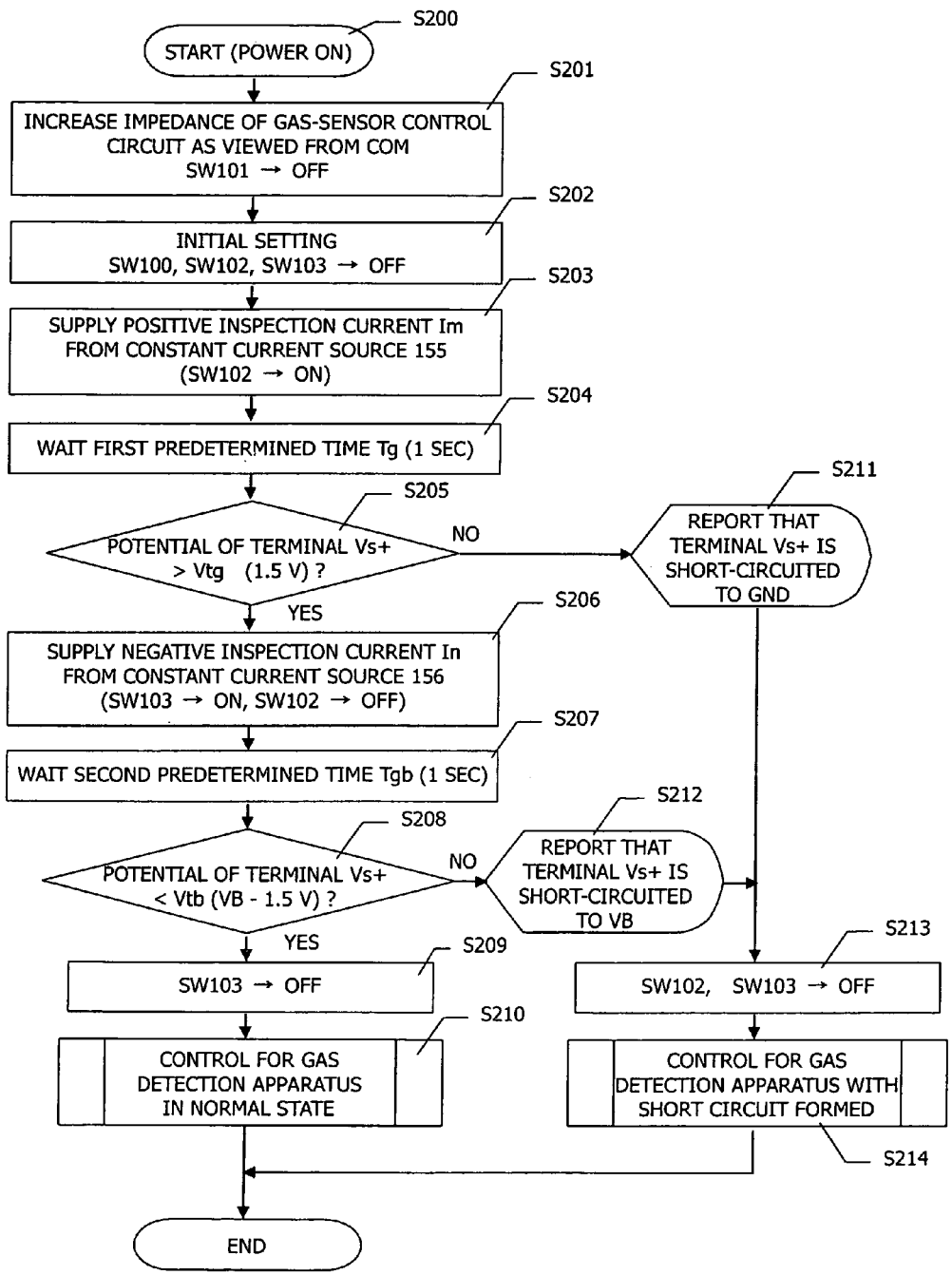
FIG. 13 is a flowchart showing the steps of an inspection method employed in Inspection Example 6 which was performed using the gas detection system of the third embodiment so as to inspect whether the first control terminal Vs+ of the gas-sensor control circuit is short-circuited to the ground potential and to then inspect whether the first control terminal Vs+ is short-circuited to the power-source potential.

Inspection for Short Circuit to the Ground Potential+Inspection for Short Circuit to the Power Source Potential Next, a change in the potential of the first control terminal Vs+ when a positive-direction inspection current Im and a negative-direction inspection current In were supplied to the first control terminal Vs+ in the gas detection system of the third embodiment, and a method for inspecting the first control terminal Vs+ by use of the gas detection system will be described with reference to FIGS. 12 and 13.

FIG. 12 is a graph showing the results of an inspection in which the positive-direction inspection current Im was supplied in order to determine whether or not the first control terminal Vs+ is short-circuited to the ground potential, and the negative-direction inspection current In was then supplied in order to determine whether or not the first control terminal Vs+ is short-circuited to the power source potential. In this graph, GND short-circuit inspection is performed in the first half, and VB short-circuit inspection is performed in the second half.

In FIG. 12, each solid line represents a change in the potential of the first control terminal Vs+ in a normal state (state in which no short circuit is formed), and each broken line represents a change in the potential of the first control terminal Vs+ at the time of formation of a short-circuit. A first half of the broken line represents a change in the potential of the first control terminal Vs+ in the case where the first control terminal Vs+ is short-circuited to the ground potential GND. A second half of the broken line represents a change in the potential of the first control terminal Vs+ in the case where the first control terminal Vs+ is short-circuited to the power source potential VB. Notably, at the time of start of inspection, the potential of the first control terminal Vs+ can assume any initial value between the power source potential VB and the ground potential GND. Therefore, the graph shows the case where the initial value is the power source potential and the case where the initial value is the ground potential.

During the GND short-circuit inspection (first half), the potential of the first control terminal Vs+ changes as follows. In the case where no short circuit is formed in the gas detection apparatus 102 and the gas detection apparatus 102 is normal, if the initial value of the potential of the first control terminal Vs+ is the ground potential GND, the potential of the first control terminal Vs+ gradually changes from the ground potential GND toward the power source potential VB with supply of the positive-direction inspection current Im. If the initial value of the potential of the first control terminal Vs+ is the power source potential VB, the potential of the first control terminal Vs+ is maintained at the power source potential VB. In contrast, if the first control terminal Vs+ is short-circuited to the ground potential GND, the potential of the first control terminal Vs+ is maintained at the ground potential GND and does not change.

During the VB short-circuit inspection (second half), the potential of the first control terminal Vs+ changes as follows. In the case where no short circuit is formed in the gas detection apparatus 102 and the gas detection apparatus 102 is normal, the potential of the first control terminal Vs+ gradually changes toward the ground potential GND. In contrast, if the first control terminal Vs+ is short-circuited to the power source potential VB, the potential of the first control terminal Vs+ is maintained at the power source potential VB and does not change.

Accordingly, in the GND short-circuit inspection, the inspection for determining whether or not the first control terminal Vs+ is short-circuited to the ground potential GND can be performed by determining whether the potential of the first control terminal Vs+ is higher than the ground-short-circuit threshold potential Vtg (1.5 V in the present example), when the first predetermined period of time Tg (1 second in the present example) has elapsed after start of supply of the positive-direction inspection current Im from the constant current source 155 to the first control terminal Vs+. Subsequently, in the VB short-circuit inspection, the inspection for determining whether or not the first control terminal Vs+ is short-circuited to the power source potential VB can be performed by determining whether the potential of the first control terminal Vs+ is lower than the power-source-short-circuit threshold potential Vtb (power source potential VB−1.5 V in the present example), when the second predetermined period of time Tgb (1 second in the present example) has elapsed after start of supply of the negative-direction inspection current In from the constant current source 156 to the first control terminal Vs+.

Next, with reference to FIG. 13, the specific steps of an inspection method performed in the gas detection system of the third embodiment will be described for the case where presence or absence of a short circuit of the first control terminal Vs+ to the ground potential GND is checked, and presence or absence of a short circuit of the first control terminal Vs+ to the power source potential VB is then checked.

First, immediately after the power of the gas detection system is turned on in step S200, the microcomputer proceeds to step S201.

In step S201, the microcomputer makes the impedance of the gas-sensor control circuit 150 high as viewed from the second control terminal COM. Specifically, the microcomputer turns the switch SW101 off. In step S202, the microcomputer turns the switches SW100, SW102, and SW103 off as an initial setting.

In step S203, the microcomputer turns the switch SW102 on so as to enable the constant current source 155 to supply the positive-direction inspection current Im (inspection current supply step). As a result, the potential of the first control terminal Vs+ changes as shown in the first half of FIG. 12, depending on whether a short-circuit is formed or not. In step S204, the microcomputer waits the first predetermined period of time Tg (1 second in the present example) by use of an unillustrated timer of the microcomputer.

In step S205, the microcomputer determines whether the potential of the first control terminal Vs+ measured by means of the potential monitor circuit 157 is higher than the ground-short-circuit threshold potential Vtg (1.5 V in the present example). Specifically, this determination is performed by comparing the ground-short-circuit threshold potential Vtg and a digital value obtained through conversion of the potential of the first control terminal Vs+ by means of the potential monitor circuit 157.

When the results of the comparison show that the potential of the first control terminal Vs+ is higher than the ground-short-circuit threshold potential Vtg (Yes), the microcomputer proceeds to step S206. Meanwhile, when the potential of the first control terminal Vs+ is not higher than the ground-short-circuit threshold potential Vtg (No), the microcomputer determines that the first control terminal Vs+ is short-circuited to the ground potential GND, and proceeds to step S211.

In step S206, the microcomputer turns the switch SW102 off so as to electrically cut off the constant current source 155 and turns the switch SW103 on so as to enable the constant current source 156 to supply the negative-direction inspection current In. As a result, the potential of the first control terminal Vs+ changes as shown in the second half of FIG. 12, depending on whether or not a short-circuit is formed.

In step S207, the microcomputer waits the second predetermined period of time Tgb (1 second in the present example) by use of an unillustrated timer of the microcomputer.

In step S208, the microcomputer determines whether the potential of the first control terminal Vs+ measured by means of the potential monitor circuit 157 is lower than the power-source-short-circuit threshold potential Vtb (power source potential VB−1.5 V in the present example). Specifically, this determination is performed by comparing the power-source-short-circuit threshold potential Vtb and the digital value of the potential of the first control terminal Vs+.

When the results of the comparison show that the potential of the first control terminal Vs+ is lower than the power-source-short-circuit threshold potential Vtb (Yes), the microcomputer determines that the first control terminal Vs+ is not short-circuited to the power source potential VB, and proceeds to step S209. Meanwhile, when the potential of the first control terminal Vs+ is not lower than the power-source-short-circuit threshold potential Vtb (No), the microcomputer determines that the first control terminal Vs+ is short-circuited to the power source potential VB, and proceeds to step S212.

In step S209, the microcomputer turns the switch SW103 off so as to electrically cut off the output of the constant current source 156.

Subsequently, in step S210, the microcomputer performs control of the gas detection system (the gas detection apparatus 102 and the gas sensor element 110) for a normal state, because the microcomputer has determined that the first control terminal Vs+, or the wiring line L1 or the first element terminal 4T1 connected thereto is not short-circuited to either the power source potential or the ground potential, and therefore, the gas detection system is normal.

Meanwhile, when a "No" determination is made in step S205, in step S211, the microcomputer reports that the first control terminal Vs+ is short-circuited to the ground potential GND, and then proceeds to step S213. When a "No" determination is made in step S208, in step S212, the microcomputer 3 reports that the first control terminal Vs+ is short-circuited to the power source potential VB, and then proceeds to step S213.

In step S213, the microcomputer turns the switches SW102 and SW103 off so as to cut off the output terminals of the constant current sources 155 and 156 from the first control terminal Vs+. Since the switch SW100 has already been turned off (step S202), the impedance of the gas-sensor control circuit 150 as viewed from the first control terminal Vs+ is also made high.

Further, in step S214, the microcomputer performs control for the case where a short circuit is formed in the gas detection apparatus 102; e.g., turning the power of the gas-sensor control circuit 150 off, and providing to a driver or the like a warning that indicates the occurrence of a short circuit by means of sound or a lamp.

In the above, the case has been described where presence or absence of a short circuit of the first control terminal Vs+ to the ground potential GND is checked, and presence or absence of a short circuit of the first control terminal Vs+ to the power source potential VB is then checked. However, these inspections can be performed in the reverse order. Further, if necessary, the inspection only for short circuit to the ground potential or the inspection only for short circuit to the power source potential can be performed.

The first through third embodiments of the present invention have been described. However, the present invention is not limited thereto, and may be practiced in a modified manner without departing from the scope of the invention.

The gas detection apparatuses of the first and second embodiments include a two-cell-type oxygen sensor element, and the gas detection apparatus of the third embodiment includes a one-cell-type oxygen sensor element. However, the present invention can be applied to gas detection apparatuses using oxygen sensor elements of other forms. Moreover, the present invention can be applied to gas detection apparatuses using gas sensor elements for detecting the concentrations of other gases such as CO, $NO_x$, $H_2$, etc.

Further, in the first through third embodiments, the gas-sensor control circuit is configured to make the impedance of the gas-sensor control circuit high, as viewed from the first control terminal Vs+ (the second control terminal COM, the third control terminal Ip+), by use of switches formed of semiconductor elements. However, the gas-sensor control circuit may be configured to make the impedance of the gas-sensor control circuit high as viewed from each control terminal by use of a three-state buffer whose output impedance can be made high through switching.

In the above-described embodiments, the gas detection system is configured to perform inspection for determining whether the first control terminal Vs+, or the wiring line L1 or the first element terminal 4T1 (110T1) electrically connected thereto, is short-circuited to the ground potential or the power source potential. However, the gas detection system may be configured to perform inspection for determining whether other terminals; e.g., the second control terminal COM, or the wiring line L2 or the second element terminal 4T2 (110T2) electrically connected thereto, is short-circuited to the ground potential or the power source potential. In this case, the second control terminal COM is a terminal to be inspected. Meanwhile, the first control terminal Vs+ and the third control terminal Ip+ (or the first control terminal Vs+) are terminals not to be inspected. Therefore, the impedance of the gas-sensor control circuit as viewed from these terminals is made high, an inspection current is supplied to the second control terminal COM in this state, and presence or absence of a short circuit is detected on the basis of a change in its potential.

In the above-described embodiments, the gas detection system is configured to perform inspection for determining whether the first control terminal Vs+ is short-circuited to the ground potential or the power source potential, because the first control terminal Vs+, the wiring line L1, and the first element terminal 4T1 (110T1) may be short-circuited to these potentials only. However, when there is a possibility that the first control terminal Vs+, the wiring line L1, and the first element terminal 4T1 (110T1) are short-circuited to different potentials, the direction and magnitude of the inspection current, the threshold potential, the predetermined waiting time before comparison and determination, etc., are properly determined in consideration of a change in the potential of the first control terminal. This change is produced upon supply of an inspection current, and varies depending on whether the control terminal is short-circuited to a different potential or whether the control terminal is not short-circuited to a different potential.

In the above-described embodiments, when a predetermined period of time (first predetermined period of time) Tg, Tb, or a second predetermined period of time Tgb, Tbg has elapsed after start of supply of inspection current to the first control terminal, the potential of the first control terminal is compared with the ground-short-circuit threshold potential Vtg or the power-source-short-circuit threshold potential Vtb so as to determine whether the first control terminal is short-circuited or not. However, the determination as to whether or not the first control terminal is short-circuited can be performed on the basis of the manner of change in the potential of the first control terminal. Specifically, the determination as to whether or not the first control terminal is short-circuited can be performed on the basis of the potential of the first control terminal as measured at a point in time before or immediately after supply of inspection current and the potential of the first control terminal as measured after a certain period of time has elapsed (i.e., the magnitude of a change in the potential between two points, or the presence or absence of such a change).

In the above-described first and second embodiments, the constant current source 43M is used as a current source for supplying the positive-direction inspection current Im, which flows out of the first control terminal Vs+. However, the constant current source 46 for supplying the bias current Icp to the gas sensor element may be used as a current source for supplying the positive-direction inspection current Im.

It should further be apparent to those skilled in the art that various changes in form and detail of the invention as shown and described above may be made. It is intended that such changes be included within the spirit and scope of the claims appended thereto.

This application is based on Japanese Patent Application No. 2005-098243 filed Mar. 30, 2005, incorporated herein by reference in its entirety.

What is claimed is:

1. A gas detection apparatus comprising:
   a gas sensor element which comprises at least one sensor cell including a solid electrolyte member and a pair of electrodes provided on opposite sides of the solid electrolyte member, and a plurality of external connection terminals electrically connected to the respective electrodes of the at least one sensor cell; and
   a gas-sensor control circuit for controlling the gas sensor element, the gas-sensor control circuit comprising a plurality of control terminals electrically connected to respective external connection terminals of the gas sensor element, an inspection current supply circuit for supplying an inspection current to an inspected terminal, which is a control terminal to be inspected for a presence or absence of a short circuit to a predetermined potential, an inspection potential measurement circuit for measuring the potential of the inspected terminal, and an uninspected terminal impedance increasing circuit for increasing the impedance of the gas-sensor control circuit as viewed from an uninspected terminal, which is a control terminal other than the inspected terminal, to electrically isolate the gas sensor element from the gas-sensor control circuit before the control terminal is inspected for the presence or absence of a short circuit to a predetermined potential.

2. The gas detection apparatus according to claim 1, wherein
   the gas sensor element includes a detection cell and a pump cell as the sensor cell, and first through third external connection terminals as the external connection terminals;
   a measurement chamber in communication with a measured space formed between the detection cell and the pump cell;
   the detection cell includes a first detection electrode facing the measurement chamber and a second detection electrode facing the first detection electrode via a solid electrolyte member, and generates a cell electromotive force in accordance with oxygen concentration within the measurement chamber;
   the pump cell includes a first pump electrode facing the measurement chamber and a second pump electrode facing the first pump electrode via a solid electrolyte member, and pumps oxygen out of the measurement chamber or pumps oxygen into the measurement chamber in accordance with current supplied thereto;

the first external connection terminal is electrically connected to the second detection electrode, the second external connection terminal is electrically connected to the first detection electrode and the first pump electrode which are electrically connected to one another, and the third external connection terminal is electrically connected to the second pump electrode; and the inspected terminal of the gas-sensor control circuit is electrically connected to the first external connection terminal, and the uninspected terminal further includes first and second uninspected terminals that are electrically connected to the second and third external connection terminals, respectively.

3. The gas detection apparatus according to claim 2, wherein the gas-sensor control circuit includes a plurality of output circuits having output terminals connected to the first and second uninspected terminals; and the uninspected terminal impedance increasing circuit comprises an output impedance increasing circuit which increases the impedance of the respective output terminals of the output circuits as viewed from the first and second uninspected terminals.

4. The gas detection apparatus according to claim 1, wherein the gas-sensor control circuit includes an output circuit having an output terminal connected to the uninspected terminal; and the uninspected terminal impedance increasing circuit comprises an output impedance increasing circuit which increases the impedance of the output terminal of the output circuit as viewed from the uninspected terminal.

5. The gas detection apparatus according to claim 1, wherein the gas-sensor control circuit includes an inspected terminal impedance increasing circuit which increases the impedance of the gas-sensor control circuit as viewed from the inspected terminal.

6. The gas detection apparatus of claim 1, wherein the uninspected terminal impedance increasing circuit increases the impedance of the gas-sensor control circuit when power to the gas-sensor control circuit is turned on.

7. The gas detection apparatus of claim 1, wherein the uninspected terminal impedance increasing circuit increases the impedance of the gas-sensor control circuit before the control terminal is inspected for a presence or absence of a short circuit.

8. A gas-sensor control circuit for controlling a gas sensor element which comprises at least one sensor cell including a solid electrolyte member and a pair of electrodes provided on opposite sides of the solid electrolyte member, and a plurality of external connection terminals electrically connected to the respective electrodes of the at least one sensor cell, the gas-sensor control circuit comprising:

a plurality of control terminals electrically connected to respective external connection terminals of the gas sensor element;

an inspection current supply circuit for supplying an inspection current to an inspected terminal, which is a control terminal to be inspected for presence or absence of a short circuit to a predetermined potential;

an inspection potential measurement circuit for measuring the potential of the inspected terminal; and an uninspected terminal impedance increasing circuit for increasing the impedance of the gas-sensor control circuit as viewed from an uninspected terminal, which is a control terminal other than the inspected terminal, to electrically isolate the gas-sensor element from the gas-sensor control circuit when the control terminal is inspected for presence or absence of a short circuit to a predetermined potential.

9. The gas-sensor control circuit according to claim 8, wherein the gas sensor element includes a detection cell and a pump cell as the sensor cell, and first through third external connection terminals as the external connection terminals;

a measurement chamber in communication with a measured space formed between the detection cell and the pump cell;

the detection cell includes a first detection electrode facing the measurement chamber and a second detection electrode facing the first detection electrode via a solid electrolyte member, and generates a cell electromotive force in accordance with oxygen concentration within the measurement chamber;

the pump cell includes a first pump electrode facing the measurement chamber and a second pump electrode facing the first pump electrode via a solid electrolyte member, and pumps oxygen out of the measurement chamber or pumps oxygen into the measurement chamber in accordance with current supplied thereto;

the first external connection terminal is electrically connected to the second detection electrode; the second external connection terminal, the first detection electrode and the first pump electrode are electrically connected to one another; and the third external connection terminal is electrically connected to the second pump electrode; and the inspected terminal is electrically connected to the first external connection terminal of the gas sensor element, and the uninspected terminal further includes first and second uninspected terminals are electrically connected to the second and third external connection terminals, respectively.

10. The gas-sensor control circuit according to claim 9, wherein the gas-sensor control circuit includes a plurality of output circuits having output terminals connected to the first and second uninspected terminals; and the uninspected terminal impedance increasing circuit comprises an output impedance increasing circuit which increases the impedance of the respective output terminals of the output circuits as viewed from the first and second uninspected terminal.

11. The gas-sensor control circuit according to claim 8, wherein the gas-sensor control circuit includes an output circuit having an output terminal connected to the uninspected terminal; and the uninspected terminal impedance increasing circuit comprises an output impedance increasing circuit which increases the impedance of the output terminal of the output circuit as viewed from the uninspected terminal.

12. The gas-sensor control circuit according to claim 8, further comprising an inspected terminal impedance increasing circuit which increases the impedance of the gas-sensor control circuit as viewed from the inspected terminal.

13. The gas detection apparatus of claim 8, wherein the uninspected terminal impedance increasing circuit increases the impedance of the gas-sensor control circuit when power to the gas-sensor control circuit is turned on.

14. The gas detection apparatus of claim 8, wherein the uninspected terminal impedance increasing circuit increases the impedance of the gas-sensor control circuit before the control terminal is inspected for a presence or absence of a short circuit.

15. A method for inspecting a gas detection apparatus which includes a gas sensor element which comprises at least one sensor cell including a solid electrolyte member and a pair of electrodes provided on opposite sides of the solid electrolyte member, and a plurality of external connection terminals electrically connected to the respective electrodes of the at least one sensor cell; and a gas-sensor control circuit for controlling the gas sensor element, the gas-sensor control circuit comprising a plurality of control terminals electrically connected to respective external connection terminals of the gas sensor element, an inspection current supply circuit for supplying an inspection current to an inspected terminal, which is a control terminal to be inspected for presence or absence of a short circuit to a predetermined potential, an inspection potential measurement circuit for measuring the potential of the inspected terminal, and an uninspected terminal impedance increasing circuit for increasing the impedance of the gas-sensor control circuit as viewed from an uninspected terminal, which is a control terminal other than the inspected terminal, to electrically isolate the gas-sensor element from the gas-sensor control circuit when the control terminal is inspected for presence or absence of a short circuit to a predetermined potential, the method comprising:
increasing the impedance of the gas-sensor control circuit as viewed from the uninspected terminal by means of the uninspected terminal impedance increasing circuit;
supplying an inspection current to the inspected terminal by means of the inspection current supply circuit; and
determining, on the basis of the potential of the inspected terminal, whether or not the inspected terminal is short-circuited to the predetermined potential.

16. The method for inspecting a gas detection apparatus according to claim 15, wherein said determining step includes waiting a predetermined period of time after the start of supply of the inspection current; and determining, after elapse of the predetermined period of time, whether or not the inspected terminal is short-circuited to the predetermined potential, based on the potential of the inspected terminal.

17. The method for inspecting a gas detection apparatus according to claim 16, wherein the determining step determines that the inspected terminal is short-circuited to the predetermined potential when the inspected terminal assumes a potential between a threshold potential and the predetermined potential after elapse of the predetermined period of time.

18. The inspection method for inspecting a gas detection apparatus according to claim 15, wherein
the inspection current supply circuit supplies an inspection current to the inspected terminal such that the potential of the inspected terminal becomes equal to a predetermined intermediate potential between the first and second predetermined potentials when the inspected terminal is not short-circuited to either the first predetermined potential or the second predetermined potential; and
the diagnosis step comprises waiting a predetermined period of time after the start of supply of the inspection current, and determining, after elapse of the predetermined period of time, whether or not the inspected terminal is short-circuited to the first predetermined potential or the second predetermined potential on the basis of the potential of the inspected terminal.

19. The method for inspecting a gas detection apparatus according to claim 18, wherein the determination step comprises determining that the inspected terminal is short-circuited to the first predetermined potential when the inspected terminal assumes a potential between a first threshold potential and the first predetermined potential after elapse of the predetermined period of time, and comprises determining that the inspected terminal is short-circuited to the second predetermined potential when the inspected terminal assumes a potential between a second threshold potential and the second predetermined potential after elapse of the predetermined period of time, wherein the second threshold potential is between the first threshold potential and the second predetermined potential.

20. The method for inspecting a gas detection apparatus according to claim 15, wherein
the gas-sensor control circuit includes an inspected terminal impedance increasing circuit which increases the impedance of the gas-sensor control circuit as viewed from the inspected terminal; and
the inspection method further comprises increasing the impedance of the gas-sensor control circuit as viewed from the inspected terminal when the inspected terminal is determined to have been short-circuited to the predetermined potential.

21. The method for inspecting a gas detection apparatus according to claim 15, wherein the uninspected terminal impedance increasing step is performed immediately after the gas-sensor control circuit is powered on.

22. A method for inspecting a gas detection apparatus which includes a gas sensor element which comprises at least one sensor cell including a solid electrolyte member and a pair of electrodes provided on opposite sides of the solid electrolyte member, and a plurality of external connection terminals electrically connected to the respective electrodes of the at least one sensor cell; and a gas-sensor control circuit for controlling the gas sensor element, the gas-sensor control circuit comprising a plurality of control terminals electrically connected to respective external connection terminals of the gas sensor element; a first inspection current supply circuit for supplying to an inspected terminal a first inspection current flowing in a first direction, the inspected terminal being a control terminal to be inspected for presence or absence of a short circuit to first and second predetermined potentials; a second inspection current supply circuit for supplying to the inspected terminal a second inspection current flowing in a second direction opposite the first direction; an inspection potential measurement circuit for measuring the potential of the inspected terminal; and an uninspected terminal impedance increasing circuit for increasing the impedance of the gas-sensor control circuit as viewed from an uninspected terminal, which is a control terminal other than the inspected terminal, to electrically isolate the gas-sensor element from the gas-sensor control circuit when the control terminal is inspected for presence or absence of a short circuit to a predetermined potential, the method comprising:
increasing the impedance of the gas-sensor control circuit as viewed from the uninspected terminal by means of the uninspected terminal impedance increasing circuit;
supplying the first inspection current to the inspected terminal by means of the first inspection current supply circuit;
determining in a first diagnosis step, on the basis of the potential of the inspected terminal to which the first inspection current has been supplied, whether or not the inspected terminal is short-circuited to the first predetermined potential;
supplying the second inspection current to the inspected terminal by means of the second inspection current supply circuit; and determining in a second diagnosis step, on the basis of the potential of the inspected terminal to which the second inspection current has been supplied, whether or not the inspected terminal is short-circuited to the second predetermined potential.

23. The method for inspecting a gas detection apparatus according to claim 22, wherein the first diagnosis step includes waiting, in a first waiting step, a first predetermined period of time after the start of supply of the first inspection current, and determining, in a first short-circuit determination step, after elapse of the first predetermined period of time, whether or not the inspected terminal is short-circuited to the first predetermined potential, on the basis of the potential of the inspected terminal; and the second diagnosis step includes waiting, in a second waiting step, a second predetermined period of time after the start of supply of the second inspection current, and determining, in a second short-circuit determination step, after elapse of the second predetermined period of time, whether or not the inspected terminal is short-circuited to the second predetermined potential, on the basis of the potential of the inspected terminal.

24. The method for inspecting a gas detection apparatus according to claim 23, wherein the first short-circuit determination step comprises determining that the inspected terminal is short-circuited to the first predetermined potential when the inspected terminal assumes a potential between a first threshold potential and the first predetermined potential after elapse of the first predetermined period of time; and the second short-circuit determination step comprises determining that the inspected terminal is short-circuited to the second predetermined potential when the inspected terminal assumes a potential between a second threshold potential and the second predetermined potential after elapse of the second predetermined period of time, wherein the second threshold potential is between the first threshold potential and the second predetermined potential.

25. The method for inspecting a gas detection apparatus according to claim 22, wherein the gas-sensor control circuit includes an inspected terminal impedance increasing circuit which increases the impedance of the gas-sensor control circuit as viewed from the inspected terminal; and the inspection method further comprises increasing the impedance of the gas-sensor control circuit as viewed from the inspected terminal when the inspected terminal is determined to have been short-circuited to the first or second predetermined potential.

26. The method for inspecting a gas detection apparatus according to claim 22, wherein the uninspected terminal impedance increasing step is performed immediately after the gas-sensor control circuit is powered on.

* * * * *